United States Patent
Roh et al.

(10) Patent No.: US 11,894,126 B1
(45) Date of Patent: Feb. 6, 2024

(54) SYSTEMS AND METHODS FOR TRACKING MOVEMENT OF A WEARABLE DEVICE FOR ADVANCED IMAGE STABILIZATION

(71) Applicant: IX Innovation LLC, Seattle, WA (US)

(72) Inventors: Jeffrey Roh, Seattle, WA (US); Justin Esterberg, Mesa, AZ (US); Adam Benson, Missoula, MT (US); Julie Benson, Missoula, MT (US); John Cronin, Jericho, VT (US); Seth Cronin, Essex Junction, VT (US); Michael John Baker, Georgia, VT (US)

(73) Assignee: IX Innovation LLC, Seattle, WA (US)

( * ) Notice: Subject to any disclaimer, the term of this patent is extended or adjusted under 35 U.S.C. 154(b) by 0 days.

(21) Appl. No.: 18/114,110

(22) Filed: Feb. 24, 2023

(51) Int. Cl.
  G16H 30/40 (2018.01)
  G06F 16/538 (2019.01)
(52) U.S. Cl.
  CPC .......... G16H 30/40 (2018.01); G06F 16/538 (2019.01)
(58) Field of Classification Search
  CPC .............................. G16H 30/40; G06F 16/538
  USPC ....................................................... 705/2–3
  See application file for complete search history.

(56) References Cited

U.S. PATENT DOCUMENTS

| | | | | |
|---|---|---|---|---|
| 2015/0253409 A1* | 9/2015 | Feiweier | .......... | G01R 33/56509 324/322 |
| 2015/0346307 A1* | 12/2015 | Beck | ................ | G01R 33/34092 324/309 |
| 2016/0245888 A1* | 8/2016 | Bollenbeck | ...... | G01R 33/56308 |
| 2016/0358334 A1* | 12/2016 | Osborne | ................ | G16H 50/30 |
| 2017/0032538 A1* | 2/2017 | Ernst | .................. | G06F 18/2415 |
| 2017/0303859 A1* | 10/2017 | Robertson | ............ | A61B 5/6819 |
| 2019/0059779 A1* | 2/2019 | Ernst | .................... | G06T 7/0012 |

* cited by examiner

*Primary Examiner* — Michael Tomaszewski
(74) *Attorney, Agent, or Firm* — Greenberg Traurig, LLP; David J. Dykeman; Andrew J. Tibbetts

(57) ABSTRACT

Disclosed are systems and methods that provide a framework for performing advanced image stabilization. The disclosed framework can operate to capture imagery used and/or relied upon for the preoperative (pre-op), operative and/or postoperative (post-op) stages of a medical procedure. The framework can function by collecting and monitoring sensor data related to a device of a user (e.g., a patient). The sensor data can be analyzed, whereby the framework can determine the most opportune time to capture an image(s)—for example, a computed tomography (CT) scan or magnetic resonance imaging (MRI) scan, and the like. Accordingly, the framework can leverage the determined capture opportunity to perform the image capture and storage of the image data and metadata, as well as perform a confidence score computation that enables validation or verification of the image's authenticity and quality.

20 Claims, 10 Drawing Sheets

600

| Wearable ID | Location | Time | Acceleration |
|---|---|---|---|
| Wearable 1 | Right Upper Chest | 3:12:01 | -0.044 |
| Wearable 1 | Right Upper Chest | 3:12:02 | -0.053 |
| Wearable 1 | Right Upper Chest | 3:12:03 | 0.015 |
| - | - | - | - |
| Wearable 2 | Left Upper Chest | 3:12:01 | -0.037 |
| Wearable 2 | Left Upper Chest | 3:12:02 | -0.042 |
| Wearable 2 | Left Upper Chest | 3:12:03 | 0.026 |
| - | - | - | - |
| Wearable 3 | Lower Abdomen | 3:12:01 | -0.038 |
| Wearable 3 | Lower Abdomen | 3:12:02 | -0.046 |
| Wearable 3 | Lower Abdomen | 3:12:03 | 0.018 |
| - | - | - | - |
| - | - | - | - |
| - | - | - | - |

| Patient ID | Wearable ID | Location | Time | Acceleration | Image Data | Confidence Score |
|---|---|---|---|---|---|---|
| JS123 | Wearable 1 | Right Upper Chest | 3:12:01 | -0.044 | JS123image1.data | 89 |
| | Wearable 2 | Left Upper Chest | 3:12:01 | -0.037 | | |
| | Wearable 3 | Lower Abdomen | 3:12:01 | -0.038 | | |
| JS123 | Wearable 1 | Right Upper Chest | 3:12:02 | -0.053 | JS123image2.data | 91 |
| | Wearable 2 | Left Upper Chest | 3:12:02 | -0.042 | | |
| | Wearable 3 | Lower Abdomen | 3:12:02 | -0.046 | | |
| JS123 | Wearable 1 | Right Upper Chest | 3:12:03 | 0.015 | JS123image3.data | 96 |
| | Wearable 2 | Left Upper Chest | 3:12:03 | 0.026 | | |
| | Wearable 3 | Lower Abdomen | 3:12:03 | 0.018 | | |
| ⋮ | ⋮ | ⋮ | ⋮ | ⋮ | ⋮ | ⋮ |

FIG. 7

SYSTEMS AND METHODS FOR TRACKING MOVEMENT OF A WEARABLE DEVICE FOR ADVANCED IMAGE STABILIZATION

This application includes material that is subject to copyright protection. The copyright owner has no objection to the facsimile reproduction by anyone of the patent disclosure, as it appears in the Patent and Trademark Office files or records, but otherwise reserves all copyright rights whatsoever.

FIELD

The present disclosure is generally related to advanced image stabilization, and more particularly, related to the computerized performance of movement tracking of a user via a wearable device for advanced image stabilization related to a medical procedure.

BACKGROUND

Many current surgical and/or medical procedures are based on and/or include the reliance upon captured imagery. The importance the captured imagery, including sets of images and/or captured video, has an effect that can impact the performance and/or success of such procedures.

SUMMARY

In some embodiments, there is provided a method for the advanced image stabilization. In some embodiments, the method includes: collecting, by a device, a first set of sensor data and a second set of sensor data using a wearable device associated with a patient, the first set of sensor data corresponding to positional movements performed by the patient during a first time period, the second set of sensor data corresponding to physical movements performed by the patient during a second time period; analyzing, by the device, the first set of sensor data and the second set of sensor data; determining, by the device, based on the analysis of the first and second sets of sensor data, a time to capture a medical image; triggering, by the device, an image capture operation to be performed by medical imaging equipment in accordance with the determined time, the medical imaging equipment connected to the device via a network, the image capture operation resulting in generation of the medical image; analyzing, by the device, the medical image; determining, by the device, a measure of quality of the medical image; and outputting, by the device, for display on a display associated with the medical imaging equipment, the medical image based on the determined measure of quality.

According to some embodiments, described herein is a system (e.g., a device) for the advanced image stabilization. The device includes at least one processor; and at least one storage medium having encoded thereon executable instructions that, when executed by the at least one processor, cause the at least one processor to carry out a method or methods similar to the methods discussed herein. According to some embodiments, such methods include: collecting, by a device, a first set of sensor data and a second set of sensor data using a wearable device associated with a patient, the first set of sensor data corresponding to positional movements performed by the patient during a first time period, the second set of sensor data corresponding to physical movements performed by the patient during a second time period; analyzing, by the device, the first set of sensor data and the second set of sensor data; determining, by the device, based on the analysis of the first and second sets of sensor data, a time to capture a medical image; triggering, by the device, an image capture operation to be performed by medical imaging equipment in accordance with the determined time, the medical imaging equipment connected to the device via a network, the image capture operation resulting in generation of the medical image; analyzing, by the device, the medical image; determining, by the device, a measure of quality of the medical image; and outputting, by the device, for display on a display associated with the medical imaging equipment, the medical image based on the determined measure of quality.

According to some embodiments, described herein is at least one non-transitory computer-readable storage medium that has tangibly stored thereon, or tangibly encoded thereon, computer readable instructions that when executed by at least one processor of a device cause the at least one processor to perform a method for advanced image stabilization. The computer-executed method, as executed from the computer-executable instructions stored on the non-transitory computer-readable storage medium, includes: collecting, by a device, a first set of sensor data and a second set of sensor data using a wearable device associated with a patient, the first set of sensor data corresponding to positional movements performed by the patient during a first time period, the second set of sensor data corresponding to physical movements performed by the patient during a second time period; analyzing, by the device, the first set of sensor data and the second set of sensor data; determining, by the device, based on the analysis of the first and second sets of sensor data, a time to capture a medical image; triggering, by the device, an image capture operation to be performed by medical imaging equipment in accordance with the determined time, the medical imaging equipment connected to the device via a network, the image capture operation resulting in generation of the medical image; analyzing, by the device, the medical image; determining, by the device, a measure of quality of the medical image; and outputting, by the device, for display on a display associated with the medical imaging equipment, the medical image based on the determined measure of quality.

According to some embodiments, the one or more systems and/or methods further include determining, based on the analysis of the first set of sensor data, positional movement data corresponding to the positional movements of the patient; analyzing the positional movement data; and determining a quantity of positional movement of the patient.

According to some embodiments, the one or more systems and/or methods further include comparing the quantity of positional movement to a movement threshold; and determining whether the patient is being repositioned during the first time period based on the comparison, where the determined time for capture is based on the determination of the patient being repositioned.

According to some embodiments, the one or more systems and/or methods further include determining, based on the analysis of the second set of sensor data, physical movement data corresponding to the physical movements of the patient; analyzing the physical movement data; and determining a pattern of the physical movements, the pattern comprising indications of an activity range of physical movements, where the determined time for capture is based on the activity range of physical movements.

According to some embodiments, the one or more systems and/or methods further include determining, based on the analysis of the medical image and/or the determined measure of quality in accordance with one or more quality criteria, whether the medical image satisfies the one or more quality criteria; and in response to determining that the medical image does not satisfy the one or more quality criteria, triggering another image capture to be performed by the medical imaging equipment to generate another medical image.

According to some embodiments, the one or more systems and/or methods further include storing, as a data entry in at least one associated database, information related to the first set of sensor data, the second set of sensor data and the captured medical image, the at least one associated database comprising a plurality of data entries for a plurality of medical images.

According to some embodiments, the one or more systems and/or methods further include extracting, from the at least one associated database, each data entry of the plurality of data entries; analyzing, for each data entry, a respective medical image; determining, for each respective medical image, a confidence score; and ranking, based on the determined confidence scores, the medical images.

According to some embodiments, the one or more systems and/or methods further include identifying, based on the ranking of medical images, a first medical image; causing display of the first medical image; and determining whether the first medical image has been approved.

In some embodiments, a second medical image within the ranking of medical images is displayed in response to determining that the first medical image has been disapproved.

In some embodiments, a set of medical images are identified and output for display.

According to some embodiments, the one or more systems and/or methods further include identifying a location of the wearable device, the location corresponding to a position on the patient, where the collection of the first and second set of sensor data is based on location data corresponding to the identified location.

According to some embodiments, the one or more systems and/or methods further include identifying a plurality of wearable devices, each wearable device of the plurality of wearable devices being positioned on a different part of the patient, where the image capture of the medical image is based on sensor data from each of the plurality of wearable devices.

In some embodiments, the medical imaging equipment is selected from a group of machines consisting of: magnetic resonance imaging (MRI), computed tomography (CT), X-ray, positron emission tomography (PET), ultrasound, angiography, fluoroscopy and myelography.

DESCRIPTIONS OF THE DRAWINGS

The features, and advantages of the disclosure will be apparent from the following description of embodiments as illustrated in the accompanying drawings, in which reference characters refer to the same parts throughout the various views. The drawings are not necessarily to scale, emphasis instead being placed upon illustrating principles of the disclosure. In the drawings:

FIG. 6 illustrates a non-limiting example of a sensor database according to some embodiments of the present disclosure;

FIG. 7 illustrates a non-limiting example of an image database according to some embodiments of the present disclosure.

DETAILED DESCRIPTION

Figure 1A:
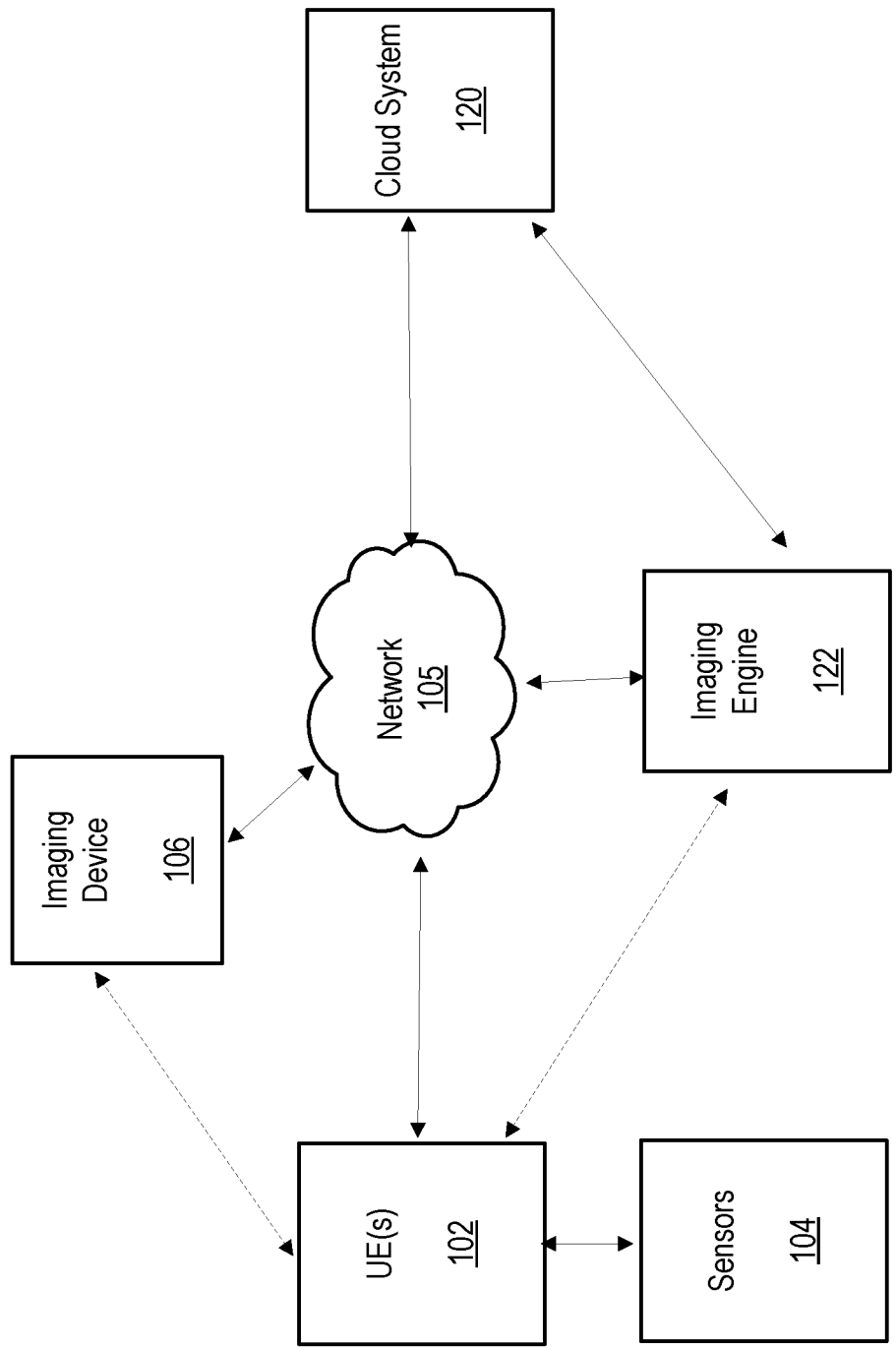
FIG. 1A is a block diagram of an example configuration within which the systems and methods disclosed herein could be implemented according to some embodiments of the present disclosure.

The present disclosure will now be described more fully hereinafter with reference to the accompanying drawings, which form a part hereof, and which show, by way of non-limiting illustration, certain example embodiments. Subject matter may, however, be embodied in a variety of different forms and, therefore, covered or claimed subject matter is intended to be construed as not being limited to any example embodiments set forth herein; example embodiments are provided merely to be illustrative. Likewise, a reasonably broad scope for claimed or covered subject matter is intended. Among other things, for example, subject matter may be embodied as methods, devices, components, or systems. Accordingly, embodiments may, for example, take the form of hardware, software, firmware or any combination thereof (other than software per se). The following detailed description is, therefore, not intended to be taken in a limiting sense.

Certain embodiments will be described in greater detail with reference to the figures. As discussed herein, the disclosed systems and methods provide a novel framework for performing advanced image stabilization. The disclosed framework can operate to capture imagery used and/or relied upon for the preoperative (pre-op), operative and/or post-operative (post-op) stages of a medical procedure. As discussed herein, implementation of the disclosed framework's functionality and capabilities can lead to more accurate and efficiently captured imagery, which can be utilized across the medical arts, as well as other areas where comprehensive image capture is relied upon and required (e.g., professional photography, and the like, for example) to perform operational tasks.

Currently, image capture technologies for medical procedures (e.g., medical images) suffer from an accuracy, quality and efficiency problem. That is, poorly focused and/or low-image quality images are not only unusable, but may also present inaccurate readings and cause an unnecessary resource expenditure. For example, when images are captured, they may be analyzed. If the user was moving during the image capture resulting in an unfocused digital representation of the user, this may result in a low/poor-quality image. Thus, the processing power and memory usage of devices analyzing the images may be strained to "make sense" of blurred or unfocused images (e.g., detect specific portions of the captured digital content in relation to a patient). Moreover, retaking images further expends resources to perform the image recapture, and leads to a reduction in available memory (e.g., more than one image set exists in memory for a single procedure/patient). Furthermore, any delay in a medical procedure, which may be caused by repetitive image capture, can cause a delay in a diagnosis for the user, and increased costs to medical institutions.

Therefore, the disclosed systems and methods provide a computerized framework for movement tracking via a wearable device(s) that enables advanced image stabilization. A user may move for a variety of reasons during a procedure, which can include, but is not limited to, heavy or natural breathing, restlessness, twitches, and/or any other type of movement that may be common during a medical imaging procedure. The disclosed framework provides mechanisms to account for such movements while producing high-quality medical images.

According to some embodiments, as discussed in more detail below, the disclosed framework functions by collecting and monitoring sensor data related to a device of a user (e.g., a wearable device worn, affixed, attached and/or held by a patient). The sensor data can be analyzed, whereby the framework can determine the most opportune time to capture an image(s)—for example, a computed tomography (CT) scan or magnetic resonance imaging (MRI) scan, and the like, as discussed below. Accordingly, in some embodiments, the disclosed framework can leverage the determined capture opportunity to perform the image capture and storage of the image data and metadata, as well as perform a confidence score computation that enables validation or verification of the image's authenticity and quality, as discussed below.

With reference to FIG. 1A, system 100 is depicted which includes user equipment (UE) 102 (e.g., a wearable device, for example), sensors 104, network 105, imaging device 106, cloud system 120 and imaging engine 122.

As discussed herein, system 100 provides functionality for advanced image stabilization. According to some embodiments, UE 102 can be any type of smart electronic device, such as, for example, an electronic device with micro-controllers that are worn close to and/or on the surface of the skin or patient's clothing, and can detect, analyze, and transmit information related to, for example body signals such as movement data, and in some embodiment's vital signs, and/or ambient data, and which allow in some embodiments, immediate biofeedback related to the wearer. In some embodiments, UE 102 can be made of and/or form a material which is easily detected by one or more imaging modalities, with or without any smart, electronic features.

Accordingly, in some embodiments, UE 102 can be any type of device, such as, but not limited to, a wearable device, mobile phone, tablet, laptop, Internet of Things (IoT) device, surgical robot, autonomous machine, and any other type of modern device. An example of UE 102 is provided below in reference to FIG. 8.

In some embodiments, system 100 may implement a single UE 102 or a set or plurality of UEs 102, which may be attached to a patient. In some embodiments, such attachment may involve the use of bands, adhesives, straps, and the like, or some combination thereof. In some embodiments a UE 102 may be implanted into the patient's body and/or their clothing. In some embodiments, UE 102 may be a reflective maker in which movement data may be tracked via an imaging device 106, as discussed infra.

In some embodiments, UE 102 can have associated therewith a plurality of sensors 104 to collect data from a patient. For example, sensors 104 may be, but are not limited to, an accelerometer or gyroscope that track a patient's movement. For example, an accelerometer may measure acceleration, which is the rate of change of the velocity of an object in meters per second squared (m/s$^2$) or in G-forces (g). Thus, for example, the collected sensor data may indicate a patient's breathing, restlessness, twitches, or other movements that may be common during a medical imaging procedure.

In some embodiments, sensors 104 may be attached and/or affixed to UE 102, and/or may be external to the UE 102, whereby they can be electronically or communicatively connected to UE 102. By way of example, UE 102 can be a fabric wrist band (or other piece of clothing) with two or more points of contrast dye that can be detected by an imaging modality (e.g., camera, MRI, CT X-Ray, and the like). For example, sensor 104 for such imaging modality may view the UE 102 and detect movement via changes in sensor data relating to the material which is readily detected by the imaging modality. In some embodiments, the imaging modality compatible material may form a pattern, shape, or other design of significance to make movement easier to detect.

For example, a contrast dye may be disposed on a non-magnetic material (e.g., cotton, polyester, and the like), such that a MRI can check for the contrast pattern, and identify X, Y, Z and motion data from the contrast pattern, as discussed herein. Accordingly, a sensor can provide movement detection functionality based on it being an attached, affixed and/or connected sensor, as well as a material and/or pattern/shape/design included within/on the material. accordingly, In some embodiments, for example, sensor functionality can be enabled via a medical imaging device (e.g. a MRI, for example), whereby a wearable can provide a salient point/point of reference for the sensor to track. In some embodiments, the wearable can be a projected pattern of light/EM that is projected on to a patient and detectable by at least one imaging modality. In some embodiments, such motion tracking can be performed via Xbox Kinect, for example.

In some embodiments, the UE 102 may include a communication device, controller, memory, power supply (e.g., a battery), and the like, to collect, analyze and transmit the collected sensors 104 data (also referred to as sensor data, interchangeably). Functionality related to such collection, analysis and transmission is discussed below at least in relation to FIG. 2, FIG. 3, FIG. 4 and FIG. 5. And, a further example of a UE 102 is discussed below in relation to FIG. 8.

According to some embodiments, as mentioned above, sensors 104 correspond to measurement tools for monitoring a characteristic, feature, attribute, value and/or metric associated with a UE 102 or patient, such as an accelerometer to measure the movements of a patient. For example, in some embodiments, sensors 104 may be discrete or part of an array or assembly, such as integrated into a catheter.

According to some embodiments, one or more of the sensors 104 may include, but are not limited to, an electrophysiologic sensor, a temperature sensor, a thermal gradient sensor, a barometer, an altimeter, an accelerometer, a gyroscope, a humidity sensor, a magnetometer, an inclinometer, an oximeter, a colorimetric monitor, a sweat analyte sensor, a galvanic skin response sensor, an interfacial pressure sensor, a flow sensor, a stretch sensor, a microphone, and the like, and/or any combination thereof.

According to some embodiments, sensors 104 may be integrated into the operation of the UE 102 in order to monitor the status of a patient. In some embodiments, the data acquired by the sensors 104 may be used to train a machine learning and/or artificial intelligence (ML/AI) algorithm used by the UE 102 and/or artificial intelligence to control the UE 102. According to some embodiments, such ML/AI can include, but are not limited to, computer vision, neural network analysis, and the like, as discussed below.

In some embodiments, sensors 104 may include an X-Ray dosimeter to monitor the intensity of X-Rays being emitted toward the patient to prevent excessive doses of radiation. In some embodiments, sensors 104 may be utilized to reduce the intensity of the X-Rays or reduce the duration or increase the interval in which the X-Rays are emitted toward the patient to control the dose throughout a procedure.

In some embodiments, sensors 104 also may track and/or collect x, y, z coordinates of UE 102 in order to detect the movements of the patient. For example, if the x, y, z coordinates of the UE 102 are rapidly moving then it may be determined that the patient is moving a lot (e.g., more than a threshold amount of movement), and capturing a quality image would be difficult; and, if the coordinates are consistent or barely changing (e.g., at or below the threshold amount) then the image can (and should) be captured due to the potential of a high-quality image.

According to some embodiments, imaging device 106 refers to a device used to acquire medical imagery. For example, imaging device 106 can effectuate image capture by any type of known or to be known mechanisms, such as, but not limited to, MRI, CT, X-ray, PET, ultrasound arthrography, angiography, fluoroscopy, myelography, and the like. Imaging device 106 may acquire images in real-time and/or be used to create composite images or models, which can also occur in real-time or near-real-time (substantially similar).

According to some embodiments, an imaging device 106 may include any device capable of detecting sound or electromagnetic waves and assembling a visual representation of the detected waves. Imaging device 106 may collect waves from any part of the electromagnetic spectrum or sounds at any range of frequencies, often as a matrix of independently acquired measurements which each representing a pixel of a two or three-dimensional (2D or 3D) image. These measurements may be taken simultaneously or in series via a scanning process or a combination of methods. Some pixels of an image produced by an imaging device 106 may be interpolated from direct measurements representing adjacent pixels in order to increase the resolution of a generated image.

Accordingly, in some embodiments, imaging device 106 may receive or generate imaging data from a plurality of imaging devices 106. An imaging device(s) 106 may include, but are not limited to, for example, cameras mounted to the ceiling or other structure above the surgical theater, cameras that may be mounted on a tripod or other independent mounting device, cameras that may be body worn by the surgeon or other surgical staff, cameras that may be incorporated into a wearable device (e.g., UE 102), such as an augmented reality device like Google® Glass, Microsoft® HoloLens, and the like, cameras that may be integrated into an endoscopic, microscopic, laparoscopic, or any camera or other imaging device 106 (e.g. ultrasound) that may be present in the surgical theater. Moreover, in some embodiments, image device 106 may also correspond to and/or be related to medical imaging equipment such as, but not limited to, MRI, CT, ultrasound, and the like.

According to some embodiments, imaging device 106 may include and/or execute any type of known or to be known ML and/or AI algorithm and/or software module capable of determining qualitative or quantitative data from medical images, which may be, for example, a deep learning algorithm that has been trained on a data set of medical images.

Figure 1B:
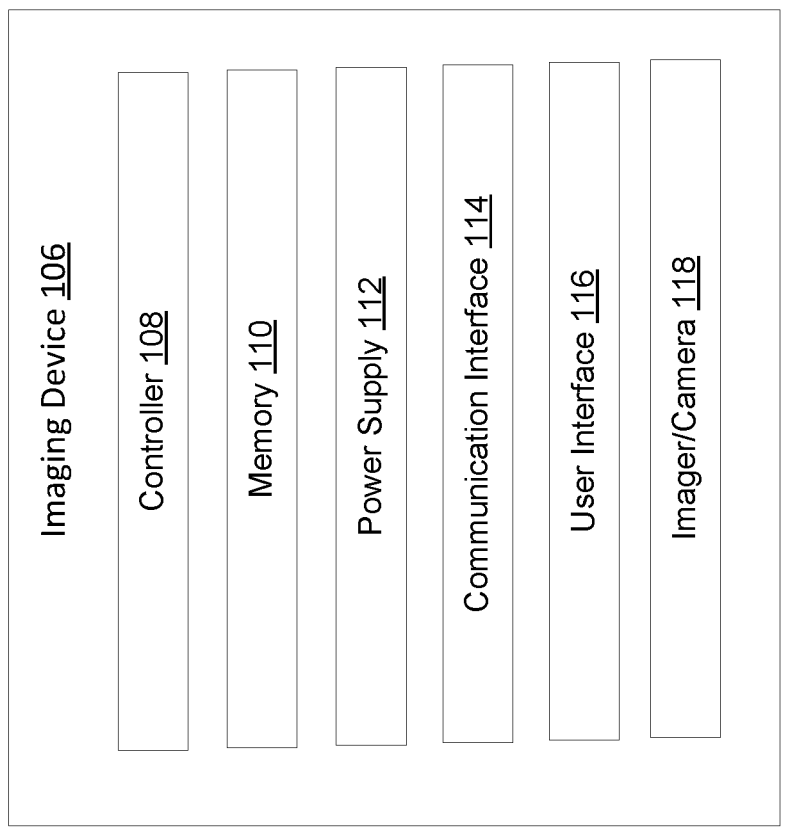
FIG. 1B and FIG. 1C are block diagrams illustrating components of exemplary systems according to some embodiments of the present disclosure.

Turning to FIG. 1B, depicted are components of an exemplary imaging device 106. Imaging device 106 can include, but is not limited to, controller 108, memory 110, power supply 112, communication interface 114, user interface (UI) 116 and imager/camera 118. It should be understood by those of skill in the art that an imaging device 106 can include additional and/or alternative components, and the disclosure of device 106 in FIG. 1B should not be construed as limiting.

According to some embodiments, a controller 108 can be a computing device that includes a processor(s) for performing computations and communicating with a memory 110 for storing data. The controller 108 can be in communication with a communications interface 114 and may further be enabled to control the imaging device 106. The controller 108 may be a commercially available central processing unit (CPU) or graphical processing unit (GPU) or may be a proprietary, purpose-build design. In some embodiments, more than one controller 108 may operate in tandem and may be of different types, such as a CPU and a GPU. According to some embodiments, a GPU may not be restricted to only processing graphics or image data, and may be configured and used for other computations.

Memory 110 is the electronic circuitry within a computing device that stores data for usage by the controller 108. The memory 110 may include persistent data storage for storing data used by the controller 108. The memory 110 may be integrated into a controller 108 or may be a discrete component. The memory 110 may be integrated into a circuit, such as soldered on component of a single board computer (SBC) or may a removable component such as a discrete dynamic random-access memory (DRAM) stick, secure digital (SD) card, flash drive, solid state drive (SSD), magnetic hard disk drive (SSD), and the like. In some embodiments, memory 110 may be part of a controller 108. Multiple types of memory 110 may be used by the imaging device 106.

Power supply 112 may be a hardware component that supplies power to an electrical device, which receives power from an electrical source (e.g., outlet) and converts the current from alternating current (AC) to direct current (DC). Power supply 112 may also regulate the voltage to an adequate amount, which allows the imaging device 106 to run smoothly without overheating. The power supply 112 may be wired or wireless, such as through a battery.

Communications interface 114 allows the imaging device 106 to communicate with external devices and may include a wireless antenna and transceiver or a port for receiving a cable to facilitate a wired connection. Non-limiting examples of a wired connection include, but are not limited to, ethernet, universal serial bus (USB) or a proprietary connection. According to some embodiments, interface 114 may include a wireless communications interface 114, which may include, but is not limited to, Wi-Fi, Bluetooth™, NFC, and/or a cellular communications interface such as 3G, 4G, LTE, or 5G.

According to some embodiments, communications interface 114 may connect a user interface 116 to the imaging device 106 or may facilitate access to a local network, such as the components of system 100 including, but not limited to, imaging engine 122, or a cloud system 120 network to access a remote server and/or database.

A user interface 116 is a mechanism of interacting with an imaging device 106 and may include any of a keyboard, computer mouse, trackball, joystick, wireless or wired gamepad, sliders, scroll wheels, touch screen or microphone for receiving voice commands. The user interface 116 may additionally include any known or to be known method of interaction of a user with imaging device 106 not specifically listed herein. In some embodiments, user interface 116 may accept direct inputs, such as from a joystick controlling the movement of a imaging device 106 or indirect inputs such as commands entered on a keyboard or touch screen such as adjusting the sensitivity of a joystick control or the speed of a imaging device 106 movement in response to a joystick.

In some embodiments, user interface 116 may also include a screen for presenting information to the user, such as, for example, a graphical user interface (GUI), patient status information, imaging data, and navigation data, and the like. In some embodiments, imaging device 106 may also include speakers (not depicted) for providing auditory feedback, and/or other mechanisms for providing haptic feedback. In some embodiments, user interface 116 may also utilize haptics to provide feedback to the user. In some embodiments, the user interface 116 may include an augmented reality (AR) or virtual reality (VR) headset to enable a surgeon to view imagery from at least one imaging device 106 in real-time and may additionally include an overlay, such as highlighting the blood vessels including a path which the catheter must be advanced to access the treatment site, such as a blood clot. The user interface 116 may additionally include voice or eye tracking controls.

In some embodiments, imager 118 or camera 118 (used interchangeably) may be the component of the imaging device 106 which is an electronic or other device that records images of something. The imager 118 may be component that produces images, such as any of various machines, for example an MRI machine, CT scanner, X-ray machine, and the like which is used to produce diagnostic images of a patient's body.

Turning back to FIG. 1A, network 105 can be any type of network, such as, but not limited to, a wireless network, cellular network, the Internet, and the like. Network 105 facilitates connectivity of the components of system 100, as illustrated in FIG. 1.

Cloud system 120 can provide for a distributed network of computers including servers and databases. In some embodiments, cloud system 120 can be any type of cloud operating platform and/or network based system upon which applications, operations, and/or other forms of network resources can be located. For example, system 122 can be a service provider and/or network provider from where applications can be accessed, sourced or executed from. In some embodiments, cloud system 120 can include a server(s) and/or a database(s) of information which is accessible over network 105. In some embodiments, a database(s) of cloud system 120 can store a dataset of data and metadata associated with local and/or network information related to a user(s) of UE 102 and the UE 102, sensors 104, imaging device 106, and the services, applications, content rendered and/or executed by UE 102 and imaging device 106.

In some embodiments, cloud system 120 may be a private cloud, where access is restricted by isolating the network such as preventing external access, or by using encryption to limit access to only authorized users. Alternatively, cloud system 120 may be a public cloud 120 where access is widely available via the internet. A public cloud 120 may not be secured or may be include limited security features.

Imaging engine 122 includes components for performing image stabilization, as discussed in more detail below at least in reference to FIGS. 2-7. Imaging engine 122 can be a special purpose machine or processor and could be hosted by UE 102. In some embodiments, engine 122 can be hosted by a peripheral device connected to UE 102—for example, a device with sensors 104.

According to some embodiments, as discussed above, imaging engine 122 can function as an application installed on UE 102, via cloud system 120 and/or imaging device 106. In some embodiments, such application can be a web-based application accessed by UE 102 over network 105 from cloud system 120 (e.g., as indicated by the connection between network 105 and engine 122, and/or the dashed line between UE 102 and engine 122 in FIG. 1A). In some embodiments, engine 122 can be configured and/or installed as an augmenting script, program or application (e.g., a plug-in or extension) to another application or program executing on UE 102, via cloud system 120 and/or imaging device 106.

Figure 1C:
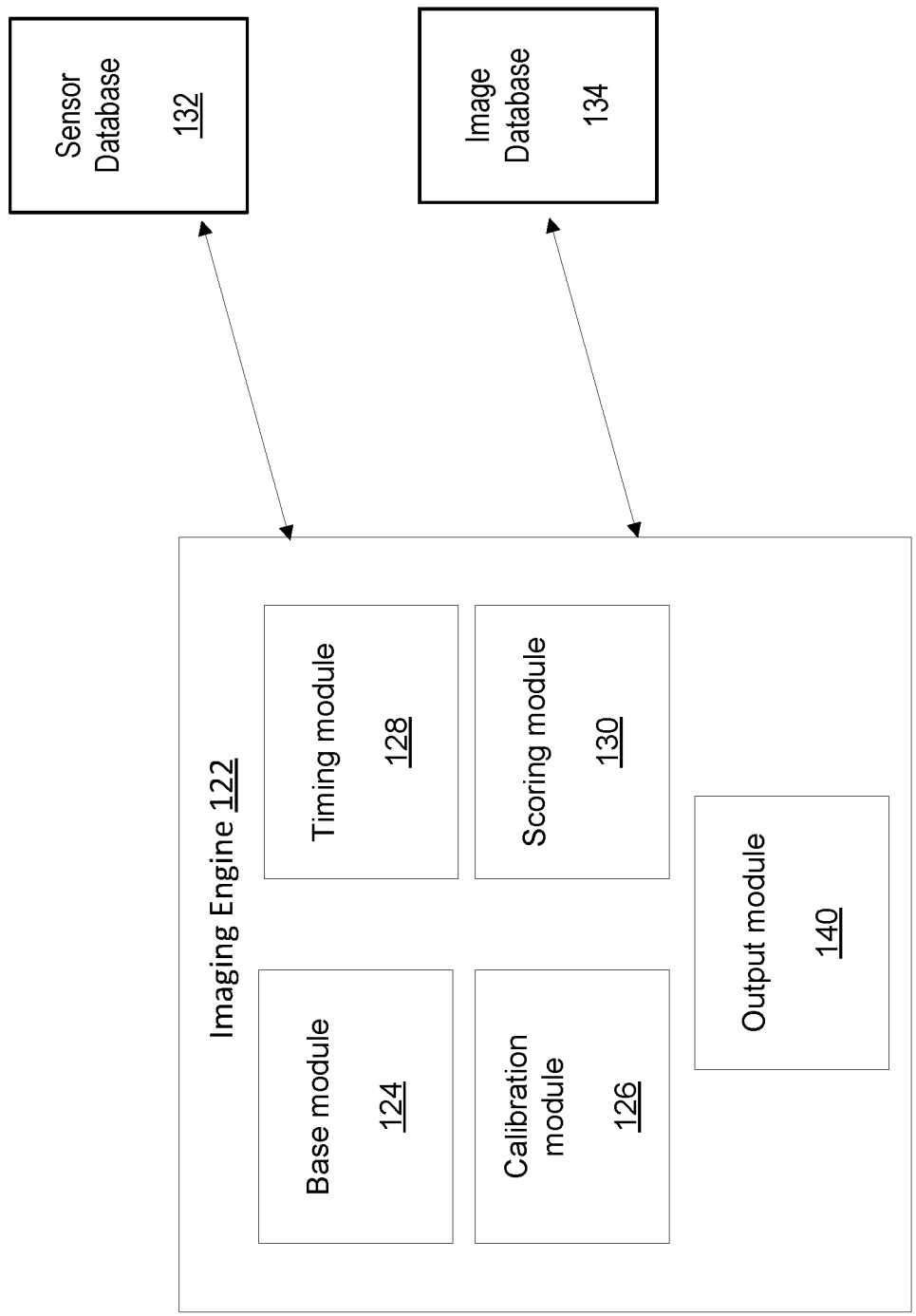

As illustrated in FIG. 1C, according to some embodiments, imaging engine 122 includes base module 124, calibration module 126, timing module 128, scoring module 130 and output module 140. It should be understood that the engine(s) and modules discussed herein are non-exhaustive, as additional or fewer engines and/or modules (or sub-modules) may be applicable to the embodiments of the systems and methods discussed.

As depicted in FIG. 1C, imaging engine 122 can be associated with sensor database 132 and/or image database 134. In some embodiments, databases 132-134 can be included within the functionality of engine 122. That is, for example, engine 122 can include a memory or memory stack that enables data structures associated with databases 132-134 to be hosted and/or remotely identified via a set of pointers or resource identifiers (uniform resource identifiers (URIs), for example). In some embodiments, databases 132-134 can be located on a network location, and accessible b engine 122. In some embodiments, databases 132-134 can be associated with cloud system 120. In some embodiments, databases 132 and/or 134 can be configured as a look-up table (LUT), blockchain and/or any other type of secure data repository.

Accordingly, in some embodiments, imaging engine 122 may collect sensor data from the UE 102, analyze the sensor data, determine when to capture an image, provide each image a confidence score to allow the user to review and approve a captured image, or some combination thereof.

In some embodiments, as discussed in more detail below, base module 124 of engine 122 can initiate the calibration module 124, the timing module 128 and the scoring module 130. In some embodiments, such initiation can be sequential and/or in parallel, as discussed in more detail below.

According to some embodiments, as discussed in more detail below in relation to FIG. 2 and FIG. 3, calibration module 126 can connect to the sensors 104, whereby sensor data and location data of the sensors can be stored in sensor database 132. The calibration module 126 displays the sensors 104 data on the user interface 116. In some embodiments, the calibration module 126 can determine if the user is repositioning the patient based on the displayed sensors 104 data. If it is determined that the user is repositioning the patient, engine 122 performs functions to enable such repositioning so that after such repositioning, engine 122 can continue monitoring, as discussed below.

In some embodiments, if/when engine 122 determines that the user is not repositioning the patient, the calibration module 126 returns to the base module 124. At this juncture, a timing module 128 can be initiated by the base module 124.

In some embodiments, as discussed in more detail below in relation to FIG. 2, FIG. 3 and FIG. 4, timing module 128 can perform periodic or continuous polling for the sensors 104 data. The timing module 128 can receive the sensors 104 data, which is then stored in the sensor database 132. According to some embodiments, timing module 128 can analyze the sensors 104 data stored in the sensor database 132, whereby based on such analysis, an image can be captured by imaging device 106. The timing module 128 stores the image data and the sensors 104 data when the image was captured in the image database 134.

According to some embodiments, timing module 128 can determine if another image is required. If it is determined that another image is required, the process returns to capturing the image. If it is determined that another image is not required, the timing module 128 returns to the base module 124.

According to some embodiments, as discussed in more detail below in relation to FIG. 2, FIG. 3, FIG. 4 and FIG. 5, scoring module 130 can be initiated by the base module 124. In some embodiments, scoring module 130 extracts the first entry in the image database 134. The scoring module 130 determines the confidence score for the image. The scoring module 130 stores the confidence score in the image database 134. The scoring module 130 determines if there are more data entries remaining in the image database 134.

According to some embodiments, if it is determined that there are more data entries remaining in the image database 134, the scoring module 130 can extract the next data entry and the process continues to determine the confidence score for that image. In some embodiments, when it is determined that there are no more data entries remaining in the image database 134, the scoring module 130 filters (or ranks) the image database 134 based on the highest confidence score. The scoring module 130 then displays the image(s) with the highest confidence score on the user interface 116.

In some embodiments, scoring module 130 can determine whether a user approved the image. If it is determined that the user did not approve the image, the scoring module 130 selects the next data entry with the next highest confidence score and the process continues to display that image on the user interface 116. If it is determined that the user approved the image, the scoring module 130 returns to the base module 124.

According to some embodiments, a sensor database 132 can include, but is not limited to, the collected sensor data from the UE(s) 102 and/or sensors 104. The data stored in database 132 may include, but is not limited to, a wearable ID, the wearable location, the time of the collected data, and the acceleration of the sensor through an accelerometer from the UE 102. A non-limiting example 600 of sensor database 132 is depicted in FIG. 6.

According to some embodiments, an image database 134 can include, but is not limited to, the sensor data from when the image was captured, the image data collected from the imaging device 106 and the confidence score from the analysis performed during the scoring module 130. In some embodiments, the data stored in database 134 may include, but is not limited to, the patient ID, the wearable ID, the location of the UE 102, the time in which the sensor data was collected, the acceleration data, the image data, such as an MRI, x-ray, CT scan, and the like, and the confidence score which is a score that indicates the clarity of the image and the lack of movement from the patient when the image was captured. A non-limiting example 700 of image database 134 is depicted in FIG. 7.

More detail of the operations, configurations and functionalities of engine 122 and each of its modules, and their role within embodiments of the present disclosure will be discussed below at least in relation to FIG. 2, FIG. 3, FIG. 4 and FIG. 5.

Figure 2:
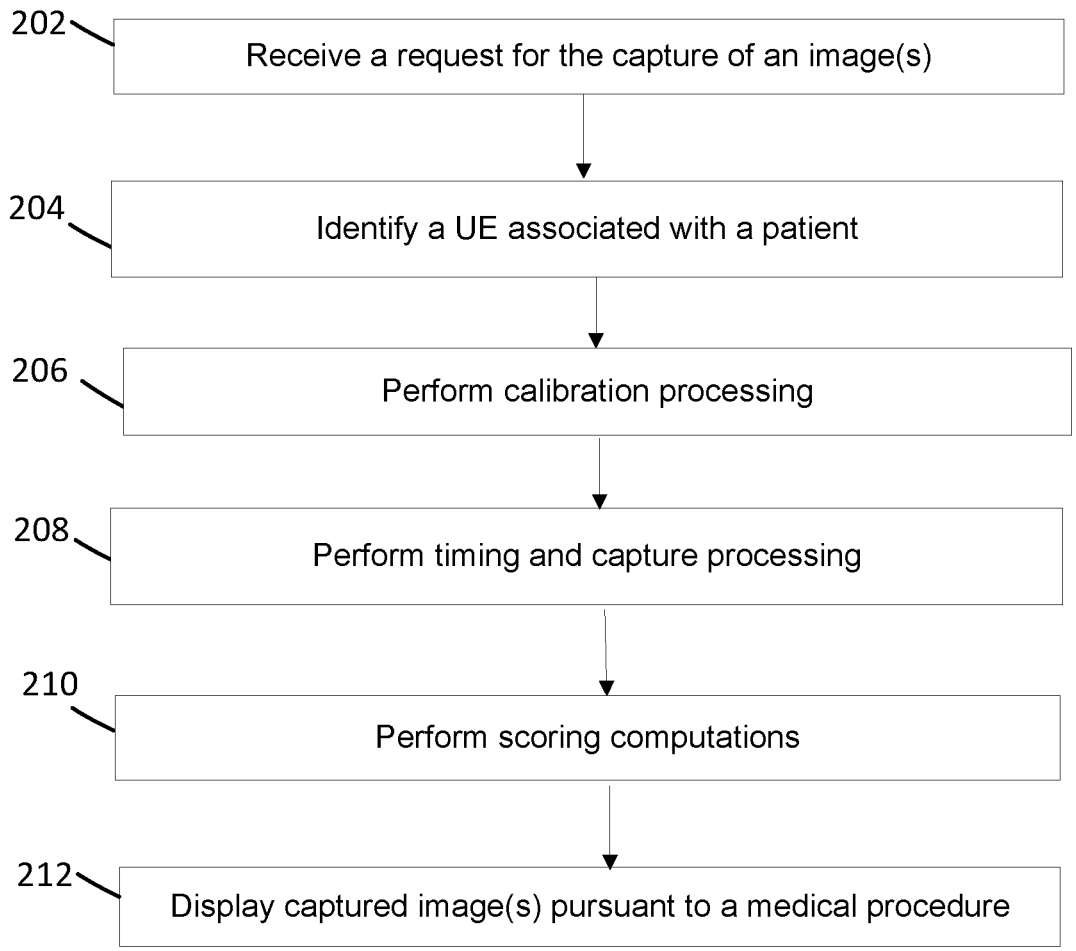
FIG. 2 illustrates an exemplary data flow according to some embodiments of the present disclosure.

FIG. 2 provides Process 200 which details embodiments for performing advanced image stabilization. According to some embodiments, Steps 202-204 of Process 200 can be performed by base module 124 of imaging engine 122; Step 206 (and sub-steps 302-318 of FIG. 3) can be performed by calibration module 126; Step 208 (and sub-steps 402-420 of FIG. 4) can be performed by timing module 128; Step 210 (and sub-steps 502-520 of FIG. 5) can be performed by scoring module 130; and Step 212 can be performed by output module 140.

According to some embodiments, Process 200 begins with Step 202 where a request to capture an image or set of images (e.g., a video) is received by engine 122. In some embodiments, the request can be provided by a user (e.g., a medical professional) respective to capturing imagery of a patient. In some embodiments, the request can correspond to preoperative planning, operative procedures and/or postoperative procedures.

It should be understood that while the discussion herein will focus on a single captured image, it should not be construed as limiting, as one of skill in the art would understand that the disclosed functionality of Process 200 and its sub-processes can be implemented for any type of image capture, which can include a set of images, video, live-streamed content, AR/VR content, and the like, without departing from the scope of the instant disclosure.

In Step 204, upon receiving the request from Step 202, engine 122 can identify the wearable device(s) associated with the patient. For example, engine 122 can identify which UE 102 is associated with the patient. In some embodiments, the identification of the UE 102 can involve, but is not limited to, detecting the number of UEs, location of the UE, connected and/or associated sensors of the UE, type of UE, and the like, or some combination thereof.

It should be understood that while the discussion herein will involve a single UE (e.g., wearable device), it should not be construed as limiting, as any number of UEs (as well as imaging devices, sensors and the like) would not alter the scope of the instant disclosure beyond the functionality disclosed herein.

In some embodiments, the identified information from Step 204 may be provided in the request of Step 202; therefore, in some embodiments, Step 204 can involve parsing the request, and determining, detecting, extracting or otherwise identifying such information from the data/metadata included in the request.

In Step 206, engine 122 executes calibration processing. As discussed herein, as provided in FIG. 3, the calibration processing performed by engine 122 in Step 206 can involve Steps 302-318, which enables the determination of whether the patient is stationary (e.g., moving at or below a threshold amount of movement) or moving beyond the threshold amount of movement. For example, if the patient is breathing normally, then this may be considered as being stationary; whereas, heavy breathing (e.g., associated with being nervous, claustrophobic, or anxious, for example) may be considered as moving.

According to some embodiments, a measured movement can correspond to particular ranges of measurements, which can include, but are not limited to, micrometer range, millimeter range, centimeter range, and the like. In some embodiments, the threshold amount of movement, and the type of measurement value associated therewith, can correspond to movements of selected points from a first position to a second position, such as an amount of movement of a selected point during a time period. The threshold for movement may vary between imaging modalities and the precision that may be obtainable from a chosen modality or the precision that may be helpful to distinguish between routine anatomical movement (e.g., breathing) and other movements such as conscious movements or spasms. The threshold may be chosen in some embodiments based on an imaging modality level of, but not limited to, accuracy/precision, accuracy/precision of data needed, size of an anatomical feature being measured (e.g., brain versus vertebra, for example), and the like, or some combination thereof.

Figure 3:
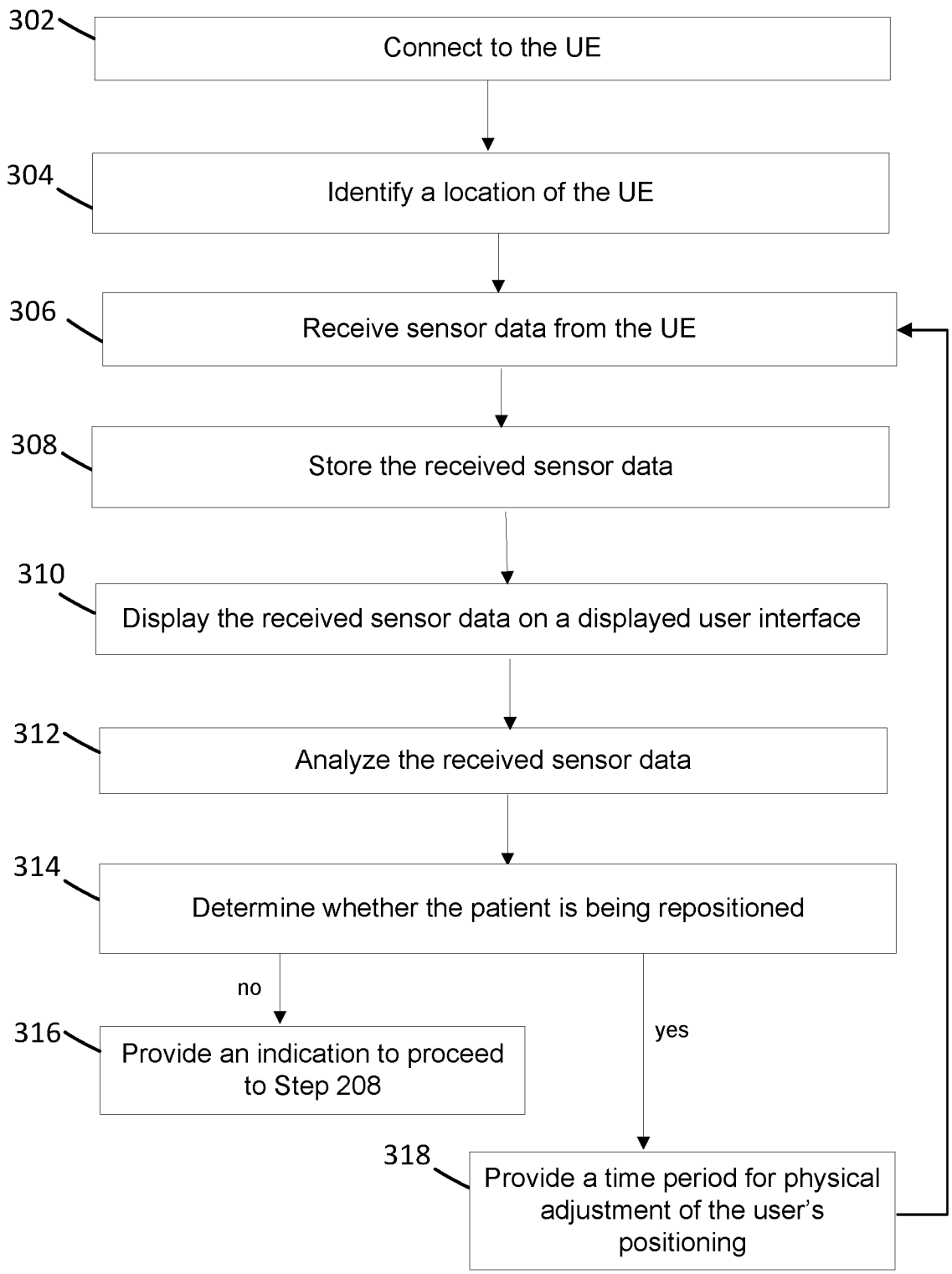
FIG. 3 illustrates an exemplary data flow according to some embodiments of the present disclosure.
Figure 4:
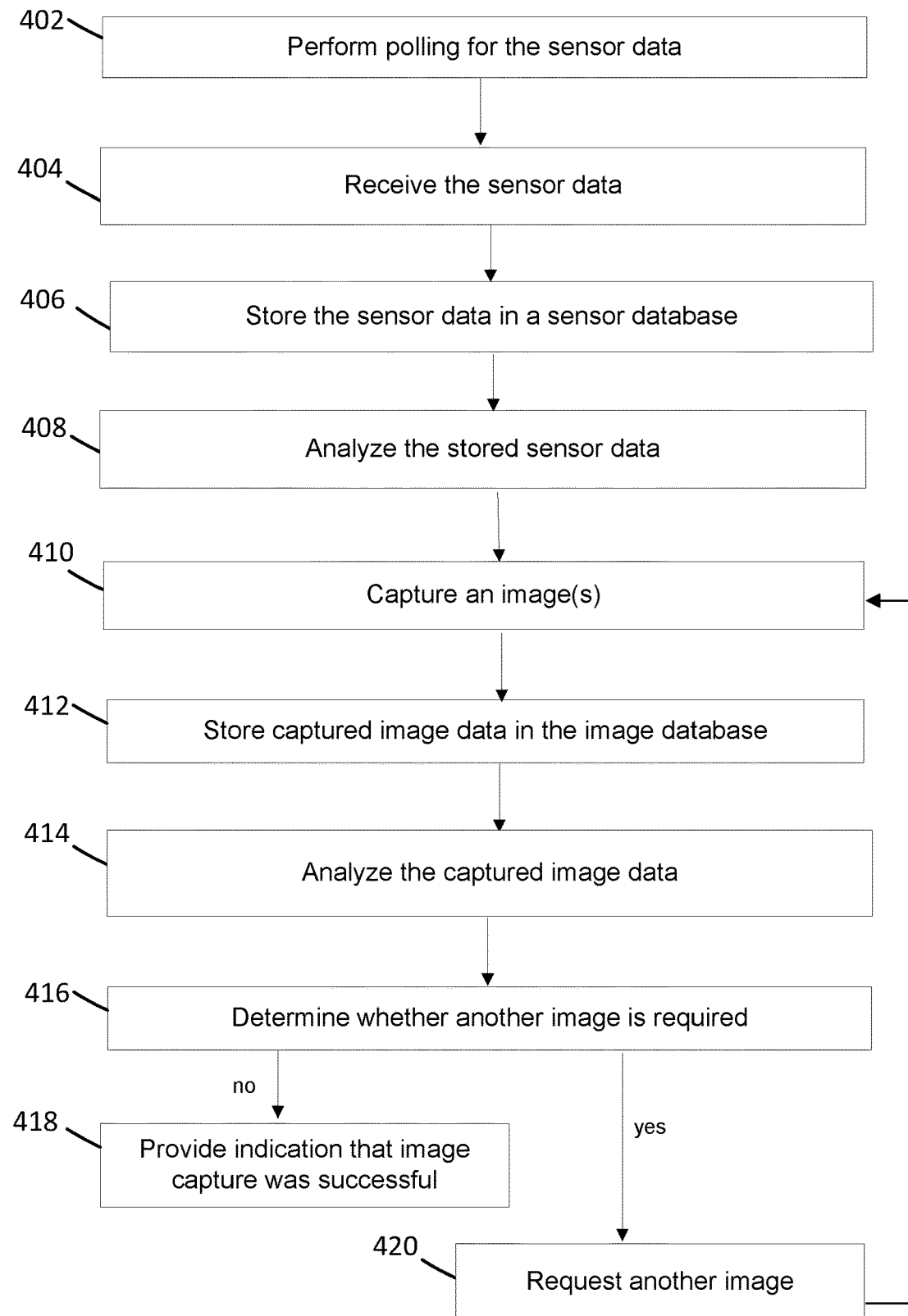
FIG. 4 illustrates an exemplary data flow according to some embodiments of the present disclosure.
Figure 5:
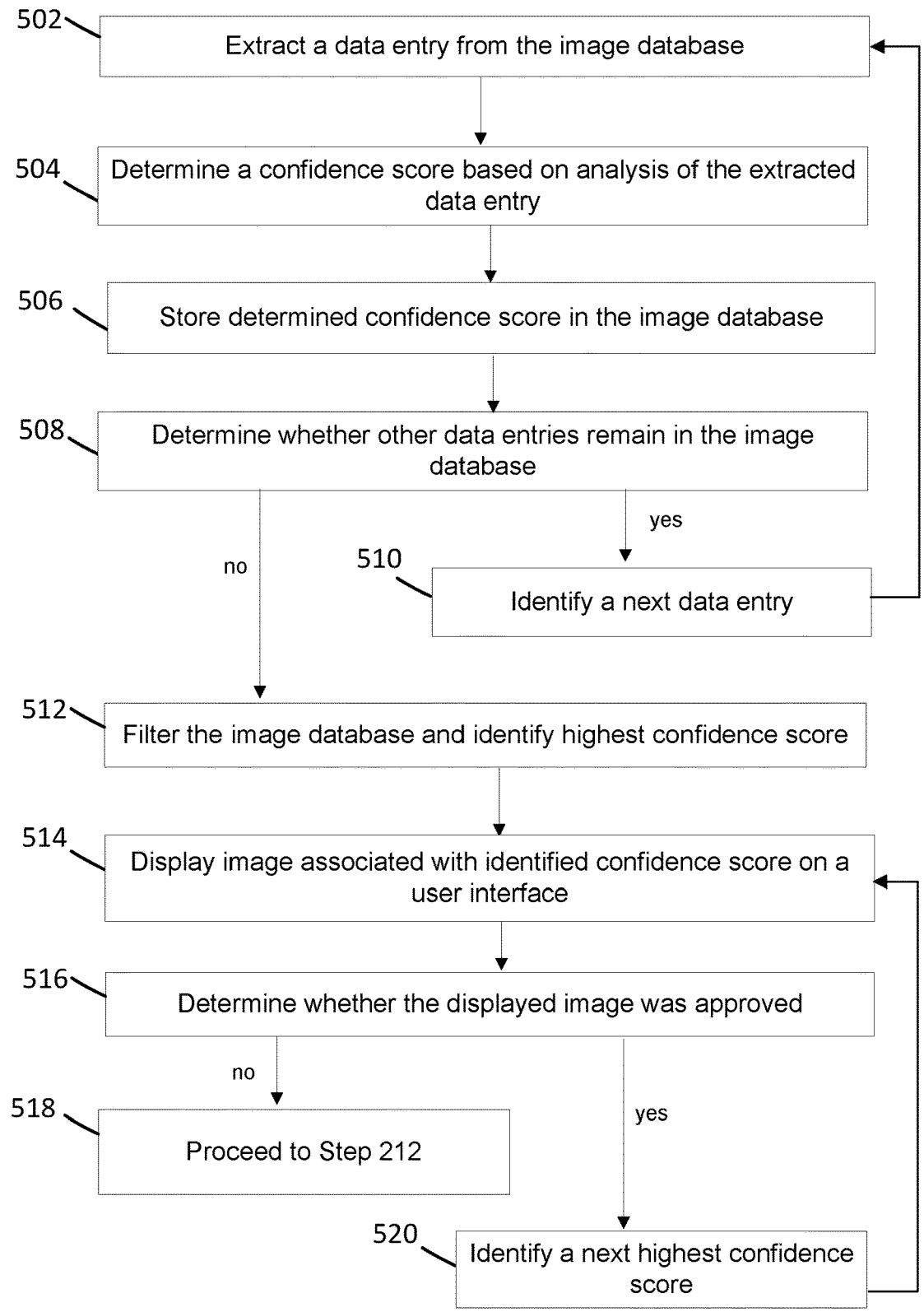
FIG. 5 illustrates an exemplary data flow according to some embodiments of the present disclosure.

Turning to FIG. 3, the processing of Step 206 begins with Step 302 where base module 124 of engine 122 initiates calibration module 126, whereby a connection is then made between engine 122 and the UE 102. In some embodiments, Step 302 can involve engine 122 connecting to the sensors 104 of the UE 102.

In some embodiments, for example, the calibration module 126 may connect to the UE 102 through the cloud system 120, a Bluetooth™ connection (e.g., BLE), a wired connection, and the like. In some embodiments, the calibration module 126 may send a signal to the UE 102 in which the wearable device confirms the connection by receiving the signal and sending back a confirmation signal to the calibration module 126 that the connection has been established.

In Step 304, engine 122 receives information related to the location of the UE 102 respective to the patient. In some embodiments, the location information can be input by a user (e.g., a medical professional, or provided by the patient), and in some embodiments, the location information can be automatically determined via location detection functionality executed by engine 122 (e.g., GPS, BLE, NFC, and the like, for example).

In some embodiments, for example, a user can input the location of the wearable device, such as the upper right chest, upper left chest, lower abdomen, and the like. In some embodiments, the location of the UE 102 may not be in view of the imaging device 106 to ensure that the UE 102 is not captured in the image and that the movements detected are close to the imaging area. In some embodiments, if the UE 102 is determined/detected to be viewable by imaging device 106, then engine 122 may output a notification that UE 102 and/or sensors 104 need to be moved.

In some embodiments, the calibration module 126 may receive location data from at least one of the sensors 104, whereby such location data may correspond to, but is not limited to, an exact or relative location of/to the patient's body, biometric data such as heart rate, respiratory rate, through a galvanic skin sensor to detect sweat, and the like, or some combination thereof.

In Step 306, the calibration module 126 of engine 122 can receive the sensor data from the UE 102. For example, the calibration module 126 receives the acceleration data (e.g., positional movement data) of the sensors 104 from the UE 102. In some embodiments, the positional movement data can correspond to a time period of collected sensor data—for example, the past n seconds which can indicate a current positional movement of the patient.

In some embodiments, the sensor data may be from any type of known or to be known sensor, such as, for example, electrophysiologic sensor, a temperature sensor, a thermal gradient sensor, a barometer, an altimeter, an accelerometer, a gyroscope, a humidity sensor, a magnetometer, an inclinometer, an oximeter, a colorimetric monitor, a sweat analyte sensor, a galvanic skin response sensor, an interfacial pressure sensor, a flow sensor, a stretch sensor, a microphone, any combination thereof, and the like.

In Step 308, calibration module 126 of engine 122 can store the UE 102 location data in the sensor database 132. For example, the calibration module 126 can store the UE 102 location data, which can indicate a position on the patient (e.g., the upper right chest, upper left chest, lower abdomen, and the like).

In Step 310, calibration module 126 of engine 122 can effectuate or cause display of the sensors 104 data on the user interface 116 of imaging device 106. For example, the calibration module 126 displays the sensors 104 data on the user interface 116 to allow a user, such as a radiologist or other type of medical professional, to determine how much movement the patient is making. For example, the acceleration data that is shown on the user interface 116 may be graph or chart that displays acceleration over time, such as time being represented on the x-axis and the acceleration being shown on the y-axis (which, for example, can be represented by $m/s^2$).

In Step 312, calibration module 126 of engine 122 can analyze the stored and displayed sensor data, and in Step 314, determine if the patient is being repositioned. For example, the user may determine that the patient is moving too much (e.g., a movement quantity, value or metric indicating movement beyond a movement threshold, as discussed above), which may be due to being uncomfortable, restlessness, breathing, and the like, and may want to reposition the patient to determine if the patient will move less in order to capture a better image. In some embodiments, the collected and computed sensor data (from Steps 308-310) can correspond to positioning movement data for the patient, and can be compared to a positioning movement threshold, whereby whether the patient should be repositioned is based therefrom.

According to some embodiments, Step 312 (and Step 314) can involve collecting a baseline representation of patient movement, which can occur prior to the processing discussed herein. In some embodiments, data associated with the baseline may be associated with, but not limited to, a particular type of patient, a particular type of imagery, a particular type of anatomy being captured, and the like, or some combination thereof. Moreover, in some embodiments, the baseline data can be provided by an imagery technician, based on determined patient patterns from previous procedures, or some combination thereof.

According to some embodiments, baseline data can be analyzed via executed statistical models to determine an amount of average amplitude and/or frequency of movement, which can include a standard deviation or variance. Thus, in some embodiments, detected movement that is determined to be outside a determined variance from an average amplitude/frequency can be interpreted by engine 122 as corresponding to a patient needing to be repositioned, as discussed herein.

According to some embodiments, such baseline data and the processing of Steps 312-314 can account for patient restlessness, which can correspond to an increase of frequency of movement (e.g., that is at or above a frequency threshold).

In some embodiments, biometric data of a patient may be utilized, which can include, but is not limited to, pulse, respiration rate, blood pressure, pupil dilatation, eye movement, and the like, or some combination thereof. Thus, for example, should such biometric data equal to or exceed a biometric threshold, then repositioning may be requested, as discussed herein.

In some embodiments, a ML/AI model/algorithm may be utilized to analyze a patient's movements (e.g., physical, amplitude, frequency and/or biometric movements and/or movement measurements, for example) against the respective thresholds in order to determine whether such movements correspond to a need for repositioning. In some embodiments, such ML/AI models can be trained via the baseline data serving as training data for such models, whereby upon performing a movement analysis (of Steps 312-314), the output can be recursively fed back so as to further train the model(s). In some embodiments, such ML/AI can include, but are not limited to, computer vision, neural network analysis, and the like.

According to some embodiments, the output from Steps 312-314 can be utilized via an image correction algorithm to remove an effect of pixel blurring. As such, in some embodiments, engine 122 can perform such image correction as a sub-process of Process 200 so as to ensure a particular quality value of a captured image, as discussed below. In some embodiments, such image correction can be utilized for movements that fall within ranges of the variation or standard deviation, as discussed above.

According to some embodiments, when it is determined that the patient is stationary (e.g., not moving beyond the positional movement threshold) and user is not repositioning the patient, the processing can proceed from Step 314 to Step 316, where an indication to proceed from Step 206 to Step 208 of Process 200 is output. For example, an indication can be displayed on UI 116 indicating that the imaging device 106 is ready for performing image capture. Accordingly, in Step 316, the user and/or patient can be alerted/notified as to an impeding image capture.

According to some embodiments, when it is determined that the patient is moving (e.g., not moving beyond the positional movement threshold) and user is (or should be) repositioning the patient, the processing can proceed from Step 314 to Step 318, where calibration module 126 can determine and/or provide a time period indication for physical adjustment of the patient. For example, such output can provide an indicator for display on UI 116 that a determined/predetermined time period must be adhered to for image capture. Accordingly, the processing can then recursively proceed from Step 318 to Step 306 to monitor the sensor data collected from UE 102 in order to further determine when the patient becomes stationary.

Turning back to FIG. 2, having performed the calibration of Step 206 (e.g., when it is determined that the patient is stationary (and/or a time of lowest movement as per a standard deviation/variation, as discussed above and in more detail below) and ready for image capture), Process 200 can proceed from Step 206 to Step 208, where timing and capture processing can be performed. Accordingly, base module 124 can initiate timing module 128 to perform the sub-steps of Step 208, as outlined in Steps 402-420 of FIG. 4.

In Step 402, timing module 128 of engine 122 performs polling for the sensor data. In some embodiments, as discussed above, such polling can be performed continuously and/or according to a predetermined time period (e.g., every 1 second, for example). For example, the timing module 128 can perform continuous polling to receive the acceleration data (e.g., physical movement data) from the accelerometer for the UE 102.

In Step 404, timing module 128 receives the sensors 104 data. For example, the timing module 128 receives the physical movement data from the sensors 104 located in the UE 102 that indicates the patient's movement. In some embodiments, the physical movement data can correspond to a time period of collected sensor data—for example, the past n seconds which can indicate a current physical movement of the patient.

In Step 406, timing module 128 can store the sensors 104 data (from Step 404) in the sensor database 132. For example, the timing module 128 stores the received data in the sensor database which can include, as discussed above, for example, the wearable ID, the wearable location, the time the data was captured and the acceleration data of the sensors 104. For example, the sensor data, such as the acceleration of the UE 102, may be recorded and stored to represent the patient's movements. The patient's movements may be recorded for a predetermined time, and the physical movement data during that time can be stored—for example, timestamps per predetermined intervals of the predetermined amount of time and the patient's movement (e.g., acceleration) data. For example, the collected sensor data may indicate a patient's breathing, restlessness, twitches, or other movements that may be common during a medical imaging procedure.

In Step 408, timing module 128 analyzes the sensors 104 data stored in the sensor database 132. For example, the timing module 128 may analyze the physical movement data of the sensor over a predetermined amount of time, such as 3 minutes, to determine if the patient is moving rapidly, which would indicate restlessness in the patient, or consistently, which may indicate the patient's breathing pattern. In some embodiments, if the patient is moving rapidly or consistently then the analysis may determine low acceleration points in the patient's movement. For example, if every 15 seconds the patient is completely still, this may indicate the ideal time to capture an image. Accordingly, the physical movement data can be compared to a physical movement threshold to provide such indication.

In some embodiments, if the patient is experiencing restlessness or rapid movements due to being in an uncomfortable setting, the analysis of Step 408 may determine the lowest acceleration point over the predetermined time, and if the acceleration data reaches the lowest acceleration point, the timing module 128 may automatically capture the image when the lowest acceleration point is achieved/detected.

In some embodiments, the timing module 128 may measure the collected x, y, z data of the patient through the sensors 104 to determine the movements of the patient in order to capture an image when the patient is still or closest to a resting point. Thus, in some embodiments, engine 122 can determine a behavior pattern of movement for the patent over a period of time, which can be leveraged to capture an image. For example, the pattern can indicate periods and/or intervals of movement, whereby when the lowest determined movement is detected and/or predicted, an image capture instruction can be provided to imaging device 106, as discussed herein.

In Step 410, based on the analysis of Step 408, timing module 128 can effectuate and/or cause the capture of the image. For example, the timing module 128 can capture the image, such as an MRI, x-ray, CT scan, and the like. The capture can correspond to a predicted and/or detected moment that involves, for example, the patient being still upon exhaling, which may be associated with a lowest acceleration point. Thus, when that lowest acceleration point is reached/detected, the timing module 128 sends a signal to the controller 108 in the imaging device 106 to activate the imager 118 through the communication interface 114.

In Step 412, timing module 128 of engine 122 can store the image data and the sensors 104 data when the image was captured in the image database 134.

According to some embodiments, the image and sensor data may be stored, then utilized to modify (e.g., correct) an image at a later time. For example, the image data may be captured and stored over a period of time, such as 200 frames over 20 milliseconds, and the sensor data may be collected and stored over the same time period in which the images were captured. Accordingly, in some embodiments, the timing module 128 may analyze an image by comparing determined difference pixel data within the images. For example, determining a difference value between the colors in each in pixel of the images to determine the difference between the images. In some embodiments, the timing module 128 may determine the time range or series of images that have the smallest difference in pixels and use corresponding sensor data, such as the acceleration data, to determine if the object in the image was at the point in time in which the object was most still. Based on this, module 128 can then use the average color of each pixel from the series of images with the smallest difference to modify an existing image stored in the image database 134 and/or create a new, corrected image that may be used later (which can also be stored in database 134).

In some embodiments, the timing module 128 may use the acceleration (physical movement) data to determine when the object captured in the image had the least amount of movement and use the series or sequence of images captured during that time period to create an average image to be sent to the scoring module 130. For example, the timing module 128 may determine the average color for each pixel in the series or sequence of images captured to create the average image. In some embodiments, the timing module 128 may determine for each image captured in a sequence a quality metric, such as the movement of the object in the image through the sensor data such as an accelerometer and identify a set of relevant images based on the quality metric and determine for each relevant image identify a reference image based on a separate image metric, such as blurriness or sharpness of the image by using the data from the pixels within the images. For example, image recognition analysis may be used to identify the object in the image, such as the type of bone from an x-ray, organ from an Mill, and the like, whereby a score can be provided to the object to determine the sharpness or lack of blurriness of the image. The reference image may be the image used by the healthcare professional to analyze and capture an image, as discussed herein.

Continuing with the processing of Step 208, upon storing the image in Step 412, timing module 128 can analyze the captured image in Step 414, and determine, in Step 416, whether another image is required.

In some embodiments, Steps 414-416 can involve engine 122 automatically determining whether the image is of a certain quality (e.g., high quality). For example, whether the features, characteristics and/or attributes (e.g., resolution, pixel count, size, dimensions, and the like) are at least a threshold satisfying value to be considered a high-quality image. Thus, in some embodiments, engine 122 can execute any type of known or to be known ML and/or AI algorithm or technology to perform computational image analysis to determine an image's quality, such as, but not limited to, computer vision, neural network analysis, full reference (FR) methods, reduced reference (RR) methods, no-reference (NR) methods, and the like. The output values of such analysis can be compared to a quality threshold to determine whether another image is required.

According to some embodiments, determinations of image quality can include, for example, determining an amount of pixel blurring. In some embodiments, pixel blurring can be detected using contrast and/or edge analysis, and determining a thickness and/or sharpness of the detected contrast or edges. In some embodiments, the thicker or smoother a transition can correspond to an increase in blur being detected.

In some embodiments, calibration markers can additionally be used, such that reproduction of specific/known patterns in acquired images can be checked. In some embodiments, engine 122 can utilize a ML model, for example, convolution, for comparing patterns of data against samples of data (e.g., a set of pixels in an image), which can be iteratively performed over each portion of an entire image. Therefore, for example, any variation from an expected pattern can be used to identify a magnitude and/or direction of an anomaly or set of anomalies impacting an image's quality.

In some embodiments, a maximum range of contrast may indicate the quality of an image, where a greater range of contrast can correlate to a higher quality.

According to some embodiments, when it is determined that another image is required, processing proceeds to Step 420, where another image request is generated, and the processing returns to Step 410. For example, the user selects a series or plurality of images to ensure that a usable or clear image is taken, and the process returns to capturing an image using the analysis that has already been performed. In some embodiments, the processing may return to collecting more sensor data (proceed from Step 420 to Step 404) to perform the analysis again to find the opportune time in which the image should be captured.

According to some embodiments, when it is determined that another image is not required, processing proceeds to Step 418, where timing module 128 to the base module 124. In Step 418, an indication is further provided to base module 124 providing an indication that a successful image capture was performed. In some embodiments, an indication can be output to UI 116 providing an indicator as to the success of a captured, high-quality image.

Turning back to Process 200 of FIG. 2, upon completing the processing of Step 208, Process 200 proceeds to Step 210 where scoring computations are performed. Accordingly, base module 124 can initiate scoring module 130 to perform the sub-steps of Step 210, as outlined in Steps 502-520 of FIG. 5.

In Step 502, scoring module 130 of engine 122 can extract a first entry from the image database 134. In some embodiments, Step 502 can involve a search query being generated, whereby a search of database 134 can be executed based therefrom. For example, the scoring module 130 extracts the first entry from the image database 134, such as the sensor data from the plurality of UEs (wearable devices) 102 and the image data.

In some embodiments, the entries in the image database 134 can correspond to the storage events discussed above at least in relation to Step 412 of FIG. 4. In some embodiments, each database entry can include information related to, but not limited to, sensor data collected respective to Steps 306-308, sensor data collected respective to Steps 404-406, the captured image (e.g., medical image) from Steps 410-414, and the like, or some combination thereof.

In Step 504, scoring module 130 can determine a confidence score for the image associated with the first entry. For example, the confidence score may be based on the acceleration data of the sensors 104 when the image was captured, where the less acceleration detected can indicate a clearer image; therefore, for this example, the confidence score would be higher than that of a less clear (or more blurry) image. For example, if the highest confidence score is 100, then there would be no acceleration from the sensors 104, therefore, if there is minimum acceleration detected, such as between 0.001 and 0.010, the confidence score can be 99.

In some embodiments, the determination or calculation performed by scoring module 130 for the confidence score may include, but is not limited to, analyzing the image data by comparing the captured image to historical images to determine the amount of characteristics, features or attributes, which can include, but are not limited to, blur, determining pixel quality, resolution, exposure time, sharpness, noise, dynamic range, tone reproduction, contrast, color, distortion, vignetting, lateral chromatic aberration, lens flare, artifacts, the effects of compressing the image data file, and the like. In some embodiments, the blur used for the confidence score may be geometric blur, detector blur, motion blur, or absorption blur.

In some embodiments, a FR method may be used to determine the quality of the image. For example, the image data may be compared to a historical image that is deemed to be of high-quality, whereby the amount of blur or clarity in the image that was taken can be determined using the historical image. In some embodiments, this can be performed via engine 122 executing an image recognition algorithm to compare the amount of objects identified in the captured image and the historical images of the same area of the body. The confidence score can be a combination of the acceleration data and the comparison to the historical image, such as, for example, minimal acceleration between 0.015 and 2% blur on the image compared to the historical image, which can provide a confidence score of 99.

In some embodiments, RR methods or NR methods may be used to determine the quality of the captured image.

In Step 506, scoring module 130 stores the determined confidence score in the image database 134. For example, the scoring module 130 can store the confidence score, such as a value or metric of 96, in the image database 134.

In Step 508, scoring module 130 determines whether there are more data entries remaining in the image database 134. For example, the scoring module 130 continuously selects the next data image in the image database 134 to assign a confidence score to every image taken during the imaging procedure.

According to some embodiments, the scoring module 130 can parse, scrape and/or mine the image database 134. When scoring module 130 determines that there are more data entries remaining in the image database 134, processing proceeds to Step 510 where a next data entry is identified, and processing returns to Step 502 for that identified data entry (e.g., determine and store the confidence score the image associated with the next identified data entry).

According to some embodiments, when scoring module 130 determines that there are no more data entries remaining in the image database 134, processing proceeds to Step 512 where scoring module 130 can filter the image database 134 and identify the highest confidence scores. For example, the scoring module 130 can filter the image database 134 by ranking each of the stored images based on their determined confidence scores. In some embodiments, such ranking can be, for example, from highest to lowest. In some embodiments, images can be grouped, whereby images with scores in a range of scores can be grouped together.

In some embodiments, upon filtering, a ranked list of images can be provided. In some embodiments, Step 512 can further involve identifying a predetermined number of images. For example, only a highest scored (or ranked) image may be identified. In some embodiments, a set of images may be identified, which can correspond to the top n images (e.g., top 3). In some embodiments, all or a portion of images with scores at or above a threshold score can be identified.

In Step 514, the images associated with the identified confidence scores can be displayed. Thus, Step 514 can involve scoring module 130 causing display of such images on the user interface 116. For example, the scoring module 130 extracts the image data from the data entry with the highest confidence score and displays the extracted image on the user interface 116 for the user to either approve or reject the image.

In Step 516, scoring module 130 determines whether the displayed image(s) was approved (e.g., did received feedback/input indicate that the user approved the image). For example, the user may either approve or reject the image. If the image is approved, then that is the image that the user can use for a procedure; and, if the image is rejected the user can be shown a next image with the next highest confidence score on the user interface 116. In some embodiments, the user may select and approve multiple images of the patient.

In some embodiments, engine 122 may automatically determine whether the image is approved without user feedback. In some embodiments, engine 122 may execute any type of known or to be known ML and/or AI algorithm or technology to perform computational image analysis to determine an image's quality, such as, but not limited to computer vision, neural network analysis, FR methods, RR methods, NR methods, and the like. Such analysis may be performed in a similar manner as discussed above in relation to Steps 414-416 of FIG. 4.

In some embodiments, engine 122 may automatically determine approval of the image based on its scoring against a score threshold. In some embodiments, when a score is above a threshold at or above a predetermined range, then that image may be automatically determined by engine 122 to be approved. For example, if the threshold is 70, and the score of the image is 99, then the 19 value differential exceeds the approval range of 15.

Therefore, according to some embodiments, when scoring module 130 determines that the image was not approved, the scoring module 130 selects, in Step 520, the next data entry with the next highest confidence score and the process continues to display the image on the user interface 116.

In some embodiments, when scoring module 130 determines that the image was approved, scoring module 130 returns, at Step 518, to the base module 124. In Step 518, processing proceeds from Step 210 to Step 212.

In Step 212, engine 122 can display the captured and approved image pursuant to the medical procedure.

By way of background, advanced surgical systems include many different types of equipment to monitor and anesthetize a patient, assist the surgeon in performing surgical tasks, and maintain the environment of the operating room.

For example, a vital signs monitor refers to medical diagnostic instruments and in particular to a portable, battery powered, multi-parametric, vital signs monitoring device that can be used for both ambulatory and transport applications, as well as bedside monitoring. These devices can be used with an isolated data link to an interconnected portable computer allowing snapshot and trended data from the monitoring device to be printed automatically and also allowing default configuration settings to be downloaded to the monitoring device. The monitoring device is capable of use as a stand-alone unit as well as part of a bi-directional wireless communications network that includes at least one remote monitoring station. A number of vital signs monitoring devices are known that are capable of measuring multiple physiologic parameters of a patient, where various sensor output signals are transmitted either wirelessly or by means of a wired connection to at least one remote site, such as a central monitoring station. According to some embodiments, a vital signs monitor can be integrated into disclosed embodiments in a variety of manners, as evident from the below discussion.

A heart rate monitor refers to the sensor(s) and/or sensor system(s) that can be applied in the context of monitoring heart rates. Embodiments are intended to measure, directly or indirectly, any physiological condition from which any relevant aspect of heart rate can be gleaned. For example, some of the embodiments measure different or overlapping physiological conditions to measure the same aspect of heart rate. Alternatively, some embodiments measure the same, different, or overlapping physiological conditions to measure different aspects of heart rate, e.g., number of beats, strength of beats, regularity of beats, beat anomalies, and the like. According to some embodiments, a heart rate monitor can be integrated into disclosed embodiments in a variety of manners (e.g., implemented via sensors 104, as discussed supra).

A pulse oximeter or SpO2 Monitor refers to a plethysmograph or any instrument that measures variations in the size of an organ or body part on the basis of the amount of blood passing through or present in the part. An oximeter is a type of plethysmograph that determines the oxygen saturation of the blood. One common type of oximeter is a pulse oximeter. A pulse oximeter is a medical device that indirectly measures the oxygen saturation of a patient's blood (as opposed to measuring oxygen saturation directly through a blood sample) and changes in blood volume in the skin. A pulse oximeter may include a light sensor that is placed at a site on a patient, usually a fingertip, toe, forehead, or earlobe, or in the case of a neonate, across a foot. Light, which may be produced by a light source integrated into the pulse oximeter, containing both red and infrared wavelengths is directed onto the skin of the patient and the light that passes through the skin is detected by the sensor. The intensity of light in each wavelength is measured by the sensor over time. The graph of light intensity versus time is referred to as the photoplethysmogram (PPG) or, more commonly, simply as the "pleth." From the waveform of the PPG, it is possible to identify the pulse rate of the patient and when each individual pulse occurs. In addition, by comparing the intensities of two wavelengths when a pulse occurs, it is possible to determine blood oxygen saturation of hemoglobin in arterial blood. This relies on the observation that highly oxygenated blood will relatively absorb more red light and less infrared light than blood with a lower oxygen saturation. According to some embodiments, a pulse oximeter can be integrated into disclosed embodiments in a variety of manners (e.g., implemented via sensors 104, as discussed supra).

An end Tidal CO2 monitor or capnography monitor refers to an instrument which is used for measurement of level of carbon dioxide (referred to as end tidal carbon dioxide, ETCO2) that is released at the end of an exhaled breath. End tidal CO2 monitor or capnography monitor is widely used in anesthesia and intensive care. ETCO2 can be calculated by plotting expiratory CO2 with time. Further, ETCO2 monitor plays a very crucial role for the measurement of applications such as cardiopulmonary resuscitation (CPR), airway assessment, procedural sedation and analgesia, pulmonary diseases such as obstructive pulmonary disease, pulmonary embolism, and the like, heart failure, metabolic disorders, and the like. The instrument can be configured as side stream (diverting) or mainstream (non-diverting). Diverting device transports, a portion of a patient's respired gases from the sampling site to the sensor while non-diverting device does not transport gas away. Also, measurement by the instrument is based on the absorption of infrared light by carbon dioxide, where exhaled gas passes through a sampling chamber containing an infrared light source and photodetector on both sides. Based on the amount of infrared light reaching the photodetector, the amount of carbon dioxide present in the gas can be calculated. According to some embodiments, an ETCO2 monitor or capnography monitor can be integrated into disclosed embodiments in a variety of manners (e.g., implemented via sensors 104, as discussed supra).

A blood pressure monitor refers to any instrument that measures blood pressure, particularly in arteries. Blood pressure monitors use a non-invasive technique (by external cuff application) or an invasive technique (by a cannula needle inserted in artery, used in operating theatre) for measurement, with non-invasive measurement being widely used. The non-invasive method (referred to as sphygmomanometer further) works by measurement of force exerted against arterial walls during ventricular systole (e.g., systolic blood pressure, occurs when heart beats and pushes blood through the arteries) and ventricular diastole (e.g., diastolic blood pressure, occurs when heart rests and is filling with blood) thereby measuring systole and diastole, respectively. It can be of three types automatic/digital, manual (aneroid-dial), and manual (mercury-column). The sphygmomanometer may include a bladder, a cuff, a pressure meter, a stethoscope, a valve, and a bulb. The cuff then inflates until it fits tightly around your arm, cutting off your blood flow, and then the valve opens to deflate it. It operates by inflating a cuff tightly around the arm, as the cuff reaches the systolic pressure, blood begins to flow around your artery, and creating a vibration which is detected by the meter, which records your systolic pressure. This systolic pressure is recorded. The techniques used for measurement may be, for example: auscultatory or oscillometric. According to some embodiments, a blood pressure monitor can be integrated into disclosed embodiments in a variety of manners (e.g., implemented via sensors 104, as discussed supra).

A body temperature monitor refers to any instrument which is used for measurement of body temperature. The instrument can measure the temperature invasively or non-invasively by placement of sensor into organs such as bladder, rectum, esophagus, tympanum, esophagus, and the like, and mouth, rectum, armpit, and the like, respectively. The sensors are of two types: contact and non-contact. It can be measured in two forms: core temperature and peripheral temperature. Temperature measurement can be done by these sensing technologies: thermocouples, resistive temperature devices (RTDs, thermistors), infrared radiators, bimetallic devices, liquid expansion devices, molecular change-of-state, and silicon diodes. A thermometer which is a commonly used instrument for the measurement of temperature consists of a temperature sensing element (e.g., temperature sensor) and a means for converting to a numerical value. According to some embodiments, a blood temperature monitor can be integrated into disclosed embodiments in a variety of manners (e.g., implemented via sensors 104, as discussed supra).

Respiration rate or breathing rate is the rate at which breathing occurs and is measured by a number of breaths a person takes per minute. The rate is usually measured when a person is at rest and simply involves counting the number of breaths for one minute by counting how many times the chest rises. Normal respiration rates for an adult person at rest are in the range: 12 to 16 breaths per minute. A variation can be an indication of an abnormality/medical condition or a patient's demographic parameters. Hypoxia is a condition with low levels of oxygen in the cells and hypercapnia is a condition in which high levels of carbon dioxide in the bloodstream. Pulmonary disorders, asthma, anxiety, pneumonia, heart diseases, dehydration, drug overdose are some of the abnormal conditions which can bring a change to the respiration rate, thereby increasing or reducing the respiration rate from normal levels. According to some embodiments, monitoring, identification and/or determination of a patient's respiratory rate can be utilized via the disclosed framework, discussed supra.

An electrocardiogram (abbreviated as EKG or ECG, interchangeably) refers to a representation of the electrical activity of the heart (graphical trace of voltage versus time) which is done by placement of electrodes on skin/body surface. The electrodes capture the electrical impulse which travels through the heart causing systole and diastole or the pumping of the heart. This impulse gives a lot of information related to the normal functioning of the heart and the production of impulses. A change may occur due to medical conditions such as arrhythmias (tachycardia where the heart rate becomes faster and bradycardia where the heart rate becomes slower), coronary heart disease, heart attacks, cardiomyopathy. The instrument used for the measurement of the electrocardiogram is called an electrocardiograph which measures the electrical impulses by the placement of electrodes on the surface of the body and represents the ECG by a PQRST waveform. PQRST wave is read as: P wave which represents the depolarization of the left and right atrium and corresponding to atrial contraction, QRS complex indicates ventricular depolarization and represents the electrical impulse as it spreads through the ventricles; T wave indicates ventricular repolarization and follows the QRS complex. According to some embodiments, an electrocardiogram can be utilized via the disclosed framework, discussed supra.

Neuromonitoring, which may also be referred to as Intraoperative neurophysiological monitoring (IONM) refers to an assessment of functions and changes in the brain, brainstem, spinal cord, cranial nerves, and peripheral nerves during a surgical procedure on these organs. It includes both continuous monitoring of neural tissue as well as the localization of vital neural structures. IONM measures changes in these organs which are indicative of irreversible damage, injuries in the organs, aiming at reducing the risk of neurological deficits after operations involving the nervous system. This has also been found to be effective in localization of anatomical structures, including peripheral nerves and sensorimotor cortex, which help in guiding the surgeon during dissection. Electrophysiological modalities which are employed in neuromonitoring are an extracellular single unit and local field recordings (LFP), somatosensory evoked potential (SSEP), transcranial electrical motor evoked potentials (TCeMEP), electromyography (EMG), electroencephalography (EEG), and auditory brainstem response (ABR). The use of neurophysiological monitoring during surgical procedures requires specific anesthesia techniques to avoid interference and signal alteration due to anesthesia. According to some embodiments, neuromonitoring can be utilized via the disclosed framework, discussed supra.

Motor evoked potential (MEP) refers to electrical signals which are recorded from descending motor pathways or muscles following stimulation of motor pathways within the brain. MEP may be calculated by measurement of the action potential which is elicited by non-invasive stimulation of the motor cortex through the scalp. MEP is a widely used technique for intraoperative monitoring and neurophysiological testing of the motor pathways specifically during spinal procedures. The technique of monitoring for measurement of MEP can be defined based on some of the parameters like a site of stimulation (motor cortex or spinal cord), method of stimulation (electrical potential or magnetic field), and site of recording (spinal cord or peripheral mixed nerve and muscle). The target site may be stimulated by the use of electrical or magnetic means. According to some embodiments, MEP can be utilized via the disclosed framework, discussed supra.

Somatosensory evoked potential (which may be abbreviated as SSEP or SEP, interchangeably) refers to the electrical signals which are elicited by the brain and the spinal cord in response to sensory stimulus or touch. SSEP is one of the most frequently used techniques for intraoperative neurophysiological monitoring in spinal surgeries. The method proves to be very reliable which allows for continuous monitoring during a surgical procedure. However, accuracy may be a concern at times in measurement. The sensor stimulus which is commonly given to the organs may be auditory, visual, or somatosensory SEPs and applied on the skin, peripheral nerves of the upper limb, lower limb, or scalp. The stimulation technique may be mechanical (widely used), or electrical (found to give larger and more robust responses), intraoperative spinal monitoring modality. According to some embodiments, somatosensory evoked potential can be utilized via the disclosed framework, discussed supra.

Electromyography (EMG) refers to the evaluation and recording of electrical signals or electrical activity of the skeletal muscles. Electromyography instrument or electromyograph or electromyogram, the instrument for the measurement of the EMG activity works on a technique used for a recording of electrical activity produced by skeletal muscles and evaluation of the functional integrity of individual nerves. The nerves which are monitored by the EMG instrument may be intracranial, spinal, or peripheral nerves. The electrodes which may be used for the acquisition of signals may be invasive and non-invasive electrodes. The technique used for measurement may be spontaneous or triggered. Spontaneous EMG refers to the recording of myoelectric signals during surgical manipulation such as compression, stretching, or pulling of nerves produces; and does not perform external stimulation. Spontaneous EMG may be recorded by the insertion of a needle electrode. Triggered EMG refers to the recording of myoelectric signals during stimulation of target site such as pedicle screw with incremental current intensities. According to some embodiments, electromyography can be utilized via the disclosed framework, discussed supra.

Electroencephalography (EEG) refers to the electrical signals in the brain. Brain cells communicate with each other through electrical impulses. EEG can be used to help detect potential problems associated with this activity. An electroencephalograph is used for the measurement of EEG activity. Electrodes ranging from 8 to 16 pairs are attached to the scalp where each pair of electrodes transmit a signal to one or more recording channels. It is one of the oldest and most commonly utilized modalities for intraoperative neurophysiological monitoring and assessing cortical perfusion and oxygenation during a variety of vascular, cardiac, and neurosurgical procedures. The waves produced by EEG are alpha, beta, theta, and delta. According to some embodiments, electroencephalography can be utilized via the disclosed framework, discussed supra.

Medical visualization systems refer to visualization systems that are used for visualization and analysis of objects (preferably three-dimensional (3D) objects). Medical visualization systems include the selection of points at surfaces, selection of a region of interest, selection of objects. Medical visualization systems may be used for applications diagnosis, treatment planning, intraoperative support, documentation, educational purpose. Medical visualization systems may consist of microscopes, endoscopes/arthroscopes/laparoscopes, fiber optics, surgical lights, high-definition monitors, operating room cameras, and the like. 3D visualization software provides visual representations of scanned body parts via virtual models, offering significant depth and nuance to static two-dimensional medical images. The software facilitates improved diagnoses, narrowed surgical operation learning curves, reduced operational costs, and shortened image acquisition times. According to some embodiments, medical visualization systems can be integrated and/or utilized via the disclosed framework, discussed supra.

A microscope refers to an instrument that is used for viewing samples & objects that cannot be seen with an unaided eye. A microscope may have components eyepiece, objective lenses, adjustment knobs, stage, illuminator, condenser, diaphragm. A microscope works by manipulating how light enters the eye using a convex lens, where both sides of the lens are curved outwards. When light reflects off of an object being viewed under the microscope and passes through the lens, it bends towards the eye. This makes the object look bigger than it is. A microscope may be of types compound (light illuminated and the image seen with the microscope is two dimensional), dissection or stereoscope (light illuminated and image seen with the microscope is three dimensional), confocal (laser-illuminated and image seen with the microscope on a digital computer screen), scanning electron (SEM, e.g., electron illuminated and image seen with the microscope in black and white), transmission electron microscope (TEM, e.g., electron illuminated and image seen with the microscope is the high magnification and high resolution). According to some embodiments, a microscope can be utilized via the disclosed framework, discussed supra.

Endoscopes or arthroscopes or laparoscopes refer to minimally invasive surgical techniques where procedures are performed by performing minimal incision in the body. An endoscope refers to an instrument to visualize, diagnose, and treat problems inside hollow organs where the instrument is inserted through natural body openings such as the mouth or anus. An endoscope may perform a procedure as follows: scope with a tiny camera attached to a long, thin tube is inserted. The doctor moves it through a body passageway or opening to see inside an organ. It can be used for diagnosis and surgery (such as for removing polyps from the colon). Arthroscope refers to an instrument to visualize, diagnose, and treat problems inside a joint by a TV camera inserted through small portals/incisions and perform procedures on cartilage, ligaments, tendons, and the like. An endoscope may perform the procedure as follows: a surgeon makes a small incision in a patient's skin and inserts a pencil-sized instrument with a small lens and lighting system to magnify the target site (joint) and viewing of the interior of the joint by means of a miniature television camera and performing procedure. Endoscope refers to an instrument to visualize, diagnose, and treat problems inside soft organs like the abdomen and pelvis by a TV camera inserted through small portals/incisions and perform procedures. According to some embodiments, endoscopes/arthroscopes/laparoscopes or minimally invasive surgery techniques can be integrated and/or utilized via the disclosed framework, discussed supra.

Fiber optics refers to flexible, transparent fiber made by drawing glass (silica) or plastic to a diameter slightly thicker than that of a human hair. Fiber optics are arranged in bundles called optical cables and used to transmit light signals over long distances. Fiber optics are used most often as a means to transmit light between the two ends of the fiber and find wide usage in the medical field. Traditional surgery requires sizable and invasive incisions to expose internal organs and operate on affected areas and with fiber optics much smaller surgical incisions can be performed. Fiber optics contain components core, cladding, buffer coating. Fiber optics may be inserted in hypodermic needles and catheters, endoscope, operation theatres, ophthalmology, dentistry tools. Fiber optics sensors include a light source, optical fiber, external transducer, and photodetector. Fiber-optic sensors may be intrinsic or extrinsic. Fiber optics sensors may be categorized into four types physical, imaging, chemical, and biological. According to some embodiments, fiber optics can be utilized via the disclosed framework, discussed supra.

Surgical lights also referred to as operating light refers to an instrument that performs illumination of a local area or cavity of the patient. Surgical lights play an important role in illumination before, during, and after a medical procedure. Surgical lights may be categorized by lamp type as conventional (incandescent) and LED (light-emitting diode). Surgical lights may be categorized by mounting configuration as ceiling-mounted, wall-mounted, or floor stand. Surgical lights may be categorized by type as tungsten, quartz, and/or xenon halogens and light-emitting diodes (LEDs). Surgical lights include sterilizable handles which allow the surgeon to adjust light positions. Some important factors affecting surgical lights may be illumination, shadow management (cast shadows and contour shadows), the volume of light, heat management, fail-safe surgical lighting. According to some embodiments, surgical lights can be utilized via the disclosed framework, discussed supra.

High-definition monitors refer to a display in which a clearer picture than possible with low-definition, low-resolution screens. High-definition monitors have a higher density of pixels per inch than past standard TV screens. Resolution for high-definition monitors may be 1280×720 pixels or more. Full HD-1920×1080, Quad HD-2560×1440, 4K-3840×2160, 8K-7680×4320 pixels. High-definition monitor may operate in progressive or interlaced scanning mode. High definition monitors used in medical applications may offer the following advantages improved visibility and allows for precise and safe surgery, rich color reproduction and provides suitable colors for each clinical discipline, better visibility, and operability with a large screen and electronic zoom, higher image quality in low light conditions, high contrast at high spatial frequencies, twice as sensitive as conventional sensors, easier determination of tissue boundaries (fat, nerves, vessels, and the like), better visualization of blood vessels and lesions. According to some embodiments, high-definition monitors can be utilized via the disclosed framework, discussed supra.

Operating room cameras refer to cameras that collect images from 360 degrees, and sensors that monitor both the operating room and people in it. Operating room cameras consist of cameras that are equipped in system and perform recording to give a bird's-eye view to the surgical team. Some cameras are on devices that surgeons insert through small incisions or orifices to see what they are doing during minimally invasive surgery. Operating room cameras may perform recording for this purpose: educational purposes: example—to broadcast a live feed of a surgical demonstration to a remote audience, to collect authentic footage for edited, instructional videos on a surgical technique or procedure; to facilitate video enhanced debriefing and coaching, or to formally assess surgical skills. According to some embodiments, operating room cameras can be utilized via the disclosed framework, discussed supra.

A surgical tower refers to an instrument used for performing minimally invasive surgery or surgery which is performed by creating small incisions in the body, therefore they are also referred to as minimally invasive devices or minimally invasive access devices. The procedure of performing minimally invasive surgery may be referred to as minimally invasive procedure or minimally invasive surgery (MIS). MIS is a safe, less invasive, and precise surgical procedure. Some of the advantages offered by surgical towers may be small incisions, less pain, low risk of infection, short hospital stays, quick recovery time, less scarring, and reduced blood loss. Some medical procedures where surgical towers are useful and are widely used may be lung procedures, gynecological, head and neck, heart, and urological conditions. MIS may be robotic or non-robotic/endoscopic. MIS may include the following: endoscopic, laparoscopic, arthroscopic, natural orifice intraluminal, and natural orifice transluminal procedures. A surgical tower access device may be designed as an outer sleeve and an inner sleeve that telescoping or slidably engages with one another. When a telescope is used to operate on the abdomen, the procedure is called laparoscopy. Surgical towers typically include access to a variety of surgical tools, such as, for example, electrocautery, radiofrequency, lasers, sensors, and the like. According to some embodiments, surgical tower can be utilized via the disclosed framework, discussed supra.

Electrocautery refers to an instrument that is used for burning a part of the body to remove or close off a part of it. Various physiological conditions or surgical procedures require the removal of body tissues and organs, a consequence of which is bleeding. In order to achieve hemostasis and for removing and sealing all blood vessels which are supplied to an organ after surgical incision an electrocautery instrument may be used. For example: after removing part of the liver for removal of tumor and the like, blood vessels in the liver must be sealed individually. An electrocautery instrument may be used for sealing living tissue such as arteries, veins, lymph nodes, nerves, fats, ligaments, and other soft tissue structures. It may be used in applications surgery, tumor removal, nasal treatment, wart removal. Electrocautery may operate in modes two monopolar or bipolar. The electrocautery instrument may consist of a generator, a handpiece, and one or more electrodes. According to some embodiments, electrocautery can be utilized via the disclosed framework, discussed supra.

RF is used in association with minimally invasive surgery devices. RF may be used for the treatment of skin by delivering it to the skin through a minimally invasive tool (fine needles) which does not require skin excision. The RF may be used for real-time tracking of minimally invasive surgery devices such as laparoscopic instruments. The RF may provide radiofrequency ablation to a patient suffering from atrial fibrillation through smaller incisions made between the ribs. The RF may be used to perform an endoscopic surgery on the body such as the spine by delivery of RF energy. According to some embodiments, radiofrequency can be utilized via the disclosed framework, discussed supra.

A laser is used in association with minimally invasive surgery devices. The laser may be used in minimally invasive surgeries with an endoscope. The laser is attached to the distal end of the endoscope and steers the laser at high speed by producing higher incision quality than existing surgical tools and minimizing damage to surrounding tissue. Laser may be used to perform minimally invasive surgeries using an endoscope, laparoscope in the lower and upper gastrointestinal tract, eye, nose, and throat. Lasers are used in minimally invasive surgery to ablate soft tissues, such as a herniated spinal disc bulge. According to some embodiments, a laser can be utilized via the disclosed framework, discussed supra.

Sensors are used in association with minimally invasive surgery devices. The sensor may be used in minimally invasive surgeries for tactile sensing of tool—tissue interaction forces. During minimally invasive surgeries field of view and workspace of tools are compromised due to the indirect access to the anatomy and lack of surgeon's hand-eye coordination. The sensors provide a tactile sensation to the surgeon by providing information of shape, stiffness, and texture of organ or tissue (different characteristics) to surgeon's hands through a sense of touch. This detection of a tumor through palpation, which exhibit a 'tougher' feel than healthy soft tissue, pulse felt from blood vessels, and abnormal lesions. The sensors may provide in output shape, size, pressure, softness, composition, temperature, vibration, shear, and normal forces. Sensor may be electrical or optical, consisting of capacitive, inductive, piezoelectric, piezoresistive, magnetic, and auditory. The sensors may be used in robotic, laparoscopic, palpation, biopsy, heart ablation, and valvuloplasty. According to some embodiments, a sensor(s) can be utilized via the disclosed framework, discussed supra (e.g., sensors 104).

Imaging systems may include instruments used for the creation of images and visualization of the interior of or metabolic functioning of a subject (e.g., a human or non-human animal, such as a human body) for diagnostic and treatment purposes. Imaging systems play a helpful role in medical settings and can help in the screening of health conditions, diagnosing causes of symptoms, monitor health conditions. Imaging systems may include various imaging techniques such as X-ray, fluoroscopy, magnetic resonance imaging (MRI), ultrasound, endoscopy, elastography, tactile imaging, thermography, medical photography, and nuclear medicine e.g., positron emission tomography (PET). Some factors which may drive the market are cost and clinical advantages of medical imaging modalities, a rising share of ageing populations, increasing prevalence of cardiovascular or lifestyle diseases, increasing demand from emerging economies. Some factors which may inhibit the market are saturation in many segments, high costs, lack of trained personnel. According to some embodiments, imaging systems can be utilized via the disclosed framework, discussed supra (e.g., imaging device 106).

X-ray may refer to a medical imaging instrument that uses X-ray radiation (e.g., X-ray range in the electromagnetic radiation spectrum) for the creation of images of the interior of the human body for diagnostic and treatment purposes. An X-ray instrument may also be referred to as an X-ray generator. It is a non-invasive instrument based on different absorption of x-rays by tissues based on their radiological density (radiological density is different for bones and soft tissues). For the creation of an image by the X-ray instrument, X-rays produced by an X-ray tube may be passed through a patient positioned to the detector. As the X-rays pass through the body, images may appear in shades of black and white, which may depend on the type of tissue the X-rays pass through and their densities. Some of the applications where X-rays are used may be bone fractures, infections, calcification, tumors, arthritis, blood vessel blockages, digestive problems, heart problems. The X-ray instrument may consist of components such as an x-ray tube, operating console, collimator, grids, detector, radiographic film, and the like. According to some embodiments, an X-ray can be utilized via the disclosed framework, discussed supra.

MRI may refer to a medical imaging instrument that uses magnets for the creation of images of the interior of the human body for diagnostic and treatment purposes. Some of the applications where MRI may be used may be brain/spinal cord anomalies, tumors in the body, breast cancer screening, joint injuries, uterine/pelvic pain detection, heart problems. For the creation of the image by an MRI instrument, magnetic resonance may be produced by magnets that produce a magnetic field that induces protons in the body to align with that field. When a radiofrequency current is then pulsed through the patient, the protons are stimulated, and spin out of equilibrium, straining against the pull of the magnetic field. Turning off the radiofrequency field allows detection of energy released by realignment of protons with the magnetic field by MRI sensors. The time taken by the protons for realignment with the magnetic field, and energy release may be dependent on environmental factors and the chemical nature of the molecules. MRI may be suitable for imaging of non-bony parts or soft tissues of the body. MRI may be less harmful as it does not use damaging ionizing radiation as in the X-ray instrument. MRI instrument may consist of magnets, gradients, radiofrequency system, computer control system. Some areas where imaging by MRI should be prohibited may be people with implants. According to some embodiments, MRI can be utilized via the disclosed framework, discussed supra.

CT may refer to a medical imaging instrument that uses an X-ray radiation (e.g., X-ray range in the electromagnetic radiation spectrum) for the creation of, for example, cross-sectional images of the interior of the human body for diagnostic and treatment purposes. CT may be a computerized x-ray imaging procedure in which a narrow beam of x-rays is aimed at a patient and quickly rotated around the body, producing signals that are processed by the machine's computer to generate cross-sectional images—or "slices"—of the body The CT instrument may produce cross-sectional images of the body. Computed tomography instrument may be different from an X-ray instrument as it creates 3-dimensional cross-sectional images of the body while X-ray creates 2-dimensional images of the body. In such a case, the 3-dimensional cross-sectional images may be created by taking images from different angles, which may be done by taking a series of tomographic images from different angles. The different taken images may be collected by a computer and digitally stacked to form a three-dimensional image of the patient. For creation of images by the CT instrument, for example, a CT scanner may use a motorized x-ray source that rotates around the circular opening of a donut-shaped structure called a gantry while the x-ray tube rotates around the patient shooting narrow beams of x-rays through the body. Some of the applications where CT may be used may be blood clots, bone fractures, including subtle fractures not visible on X-ray, organ injuries. According to some embodiments, CT can be utilized via the disclosed framework, discussed supra.

Stereotactic navigation systems refer to an instrument that uses patient imaging (e.g., CT, Mill) to guide surgeons in the placement of specialized surgical instruments and implants before and during a procedure. The patient images are taken to guide the physician before or during the medical procedure. The stereotactic navigation system includes a camera having infrared sensors to determine the location of the tip of the probe being used in the surgical procedure. This information is sent in real-time so that the surgeons have a clear image of the precise location of where they are working in the body. Stereotactic navigation systems may be framed (attachment of a frame to patient's head using screws or pins) or frameless (do not require the placement of a frame on the patient's anatomy). Stereotactic navigation systems may be used for diagnostic biopsies, tumor resection, bone preparation/implant placement, placement of electrodes, otolaryngologic, or neurosurgical procedures. According to some embodiments, stereotactic navigation systems can be utilized via the disclosed framework, discussed supra.

Ultrasound imaging also referred to as sonography or ultrasonography refers to a medical imaging instrument that uses ultrasound or sound waves (also referred to as acoustic waves) for the creation of cross-sectional images of the interior of the human body for diagnostic and treatment purposes. Ultrasound in the instrument may be produced by a piezoelectric transducer which produces sound waves and sends them into the body. The sound waves which are reflected are converted into electrical signals which are sent to an ultrasound scanner. Ultrasound instruments may be used for diagnostic and functional imaging. Ultrasound instruments may be used for therapeutic or interventional procedures. Some of the applications where ultrasound may be used are diagnosis/treatment/guidance during medical procedures e.g., biopsies, internal organs such as liver/kidneys/pancreas, fetal monitoring, and the like, in soft tissues, muscles, blood vessels, tendons, joints. Ultrasound may be used for internal (transducer is placed in organs e.g., vagina) and external (transducer is placed on chest for heart monitoring or abdomen for the fetus). An ultrasound machine may consist of a monitor, keyboard, processor, data storage, probe, and transducer. According to some embodiments, an ultrasound can be utilized via the disclosed framework, discussed supra.

An anesthesiology machine refers to a machine that is used to generate and mix medical gases like oxygen or air and anesthetic agents to induce and maintain anesthesia in patients. Anesthesiology machines deliver oxygen and anesthetic gas to the patient as well as filter out expiratory carbon dioxide. Anesthesia machine may perform following functions provides O2, accurately mix anesthetic gases and vapors, enable patient ventilation, and minimize anesthesia related risks to patients and staff. Anesthesia machine may consist of the following essential components a source of oxygen (O2), O2 flowmeter, vaporizer (anesthetics include isoflurane, halothane, enflurane, desflurane, sevoflurane, and methoxyflurane), patient breathing circuit (tubing, connectors, and valves), scavenging system (removes any excess anesthetics gases). Anesthesia machine may be divided into three parts: the high-pressure system, the intermediate pressure system, and the low-pressure system. The process of anesthesia starts with oxygen flow from pipeline or cylinder through the flowmeter, O2 flows through the vaporizer and picks up the anesthetic vapors, the O2-anesthetic mix then flows through the breathing circuit and into the patient's lungs, usually by spontaneous ventilation or normal respiration. The O2-anesthetic mix then flows through the breathing circuit and into the patient's lungs, usually by spontaneous ventilation or normal respiration. According to some embodiments, an anesthesiology machine can be utilized via the disclosed framework, discussed supra.

A surgical bed is a bed equipped with mechanisms that can elevate or lower the entire bed platform, flex, or extend individual components of the platform, or raise or lower the head or the feet of the patient independently. Surgical bed may be an operation bed, cardiac bed, amputation Bed, fracture bed. Some essential components of a surgical bed may be bed sheet, woolen blanket, bath towel, bed block. Surgical beds can also be referred to as a postoperative bed, refers to a special type of bed made for the patient who is coming from the operation theatre or from another procedure that requires anesthesia. The surgical bed is designed in a manner that makes it easier to transfer an unconscious or weak patient from a stretcher/wheelchair to the bed. The surgical bed should protect bed linen from vomiting, bleeding, drainage, and discharges, provide warmth and comfort to the patient to prevent shock, provide necessary position, which is suitable for operation, protect patient from being chilled, prepared to meet any emergency. According to some embodiments, a surgical bed can be utilized via the disclosed framework, discussed supra.

A disposable air warmer (also referred to as bair, used interchangeably) refers to a convective temperature management system used in a hospital or surgery center to maintain a patient's core body temperature. The instrument consists of a reusable warming unit and a single-use disposable warming blankets for use during surgery and may also be used before and after surgery. The air warmer uses convective warming consisting of two components a warming unit and a disposable blanket. The air warmer filter air and then force warm air through disposable blankets which cover the patient. The blanket may be designed to use pressure points on the patient's body to prevent heat from reaching areas at risk for pressure sores or burns. The blanket may also include drain holes where fluid passes through the surface of the blanket to linen underneath which will reduce the risk of skin softening and reduce the risk of unintended cooling because of heat loss from evaporation. According to some embodiments, a disposable air warmer can be utilized via the disclosed framework, discussed supra.

A sequential compression device (SVD) refers to an instrument that is used to help prevent blood clots in the deep veins of legs. The sequential compression device use cuffs around the legs that fill with air and squeeze your legs. This increases blood flow through the veins of your legs and helps prevent blood clots. A deep vein thrombosis (DVT) is a blood clot that forms in a vein deep inside the body. Some of the risks of using a DVT may be discomfort, warmth, or sweating beneath the cuff, skin breakdown, nerve damage, pressure injury. According to some embodiments, a sequential compression device(s) can be utilized via the disclosed framework, discussed supra.

A Jackson frame refers to a frame or table which is designed for use in spine surgeries and may be used in a variety of spinal procedures in supine, prone, lateral positions in a safe manner. Two peculiar features of the Jackson table are no central table support and its ability to rotate the table through 180 degrees. The Jackson table is supported at both ends keeping the whole of the table free. This allows the visualization of trunk and major parts of extremities as well. The Jackson frame allows the patient to be slid from the cart onto the table in the supine position with appropriate padding placed. The patient is then strapped securely on the table. According to some embodiments, the Jackson frame can be utilized via the disclosed framework, discussed supra.

A bed position controller refers to an instrument for controlling the position of the patient bed. Positioning a patient in bed is important for maintaining alignment and for preventing bedsores (pressure ulcers), foot drop, and contractures. Proper positioning is also vital for providing comfort for patients who are bedridden or have decreased mobility related to a medical condition or treatment. When positioning a patient in bed, supportive devices such as pillows, rolls, and blankets, along with repositioning, can aid in providing comfort and safety. The patient may be in the following positions in a bed supine position, prone position, lateral position, sims position, fowler's position, semi-Fowler's position, orthopedic or tripod position, Trendelenburg position. According to some embodiments, a bed position controller can be utilized via the disclosed framework, discussed supra.

Operating room environmental controls refer to control or maintenance of the environment in an operation theatre where procedures are performed to minimize the risk of airborne infection and provide a conducive environment for everyone in the operation theatre-surgeon, anesthesiologist, nurses & patient). Some factors which may contribute to poor quality in the environment of the operating room are temperature, ventilation, and humidity and they can lead to profound effects on the health of people in the operating room and work productivity. As an example: surgeons prefer a cool, dry climate since they work in bright, hot lights; anesthesia personnel prefer a warmer, less breezy climate; patient condition demands a relatively warm, humid, and quiet environment. Operating room environmental controls may control the environment by taking care of the following factors environmental humidity, infection, odor control. Humidity control may be done by controlling the temperature of anesthesia gases; Infection can be controlled by the use of filters to purify the air. According to some embodiments, operating room environmental controls can be utilized via the disclosed framework, discussed supra.

Heating, ventilation, and air conditioning (HVAC) refers to a system for regulating environment of indoor settings by moving air between indoor and outdoor areas, along with heating and cooling. HVAC may use a different combination of systems, machines, and technologies to improve comfort. HVAC may be necessary to maintain the environment of an operating room. HVAC for an operating room may be a traditional operating room (which may have a large diffuser array directly above the operating table) or a hybrid operating room (which may have monitors and imaging equipment that consume valuable ceiling space and complicate the design process). HVAC may consist of three main units heating unit (it may be a furnace or a boiler), a ventilation unit (it may be natural or forced), and an air conditioning unit (which may remove existing heat). HVAC may be made of components as air return, filter, exhaust outlets, ducts, electrical elements, outdoor unit, compressor, coils, and blower. The HVAC system may use central heating and AC systems that use a single blower to circulate air via internal ducts. According to some embodiments, a HVAC system(s) can be utilized via the disclosed framework, discussed supra.

Air purification refers to a system for removing contaminants from the air in a room to improve indoor air quality. Air purification may be important in an operating room as surgical site infection may be a reason for high mortality and morbidity. The air purification system may deliver clean, filtered, contaminant-free air over the operating room table with diffuser, airflow, and the like, to remove all infectious particles down and away from the patient. Air purification system may be air curtain, multi-diffuser array, or single large diffuser (based on laminar diffuser flow) or high-efficiency particulate air filter. high-efficiency particulate air filter referred to as HEPA filter protects from infection and contamination by a filter which is mounted at the terminal of the duct. HEPA filter may be mounted on the ceiling and deliver clean, filtered air in a flow to the room that provides a sweeping effect that pushes contaminants out via the return grilles that are usually mounted on the lower wall. According to some embodiments, air purification can be utilized via the disclosed framework, discussed supra.

Orthopedic tools, also referred to as orthopedic instruments (used interchangeably), can be used for treatment and prevention of deformities and injuries of musculoskeletal system or skeleton, articulations, and locomotive system (e.g., set formed by skeleton, muscles attached to it and part of nervous system which controls the muscles). Major percentage of orthopedic tools are made of plastic. Orthopedic tools may be divided into the following specialties hand and wrist, foot and ankle, shoulder and elbow, arthroscopy, hip, and knee. Orthopedic tool may be fixation tools, relieving tools, corrective tools, compression-distraction tools. Fixation tool refers to a tool designed to restrict movements partially or completely in a joint, e.g., hinged splints (for preserving a certain range of movement in a joint), rigid splints. Relieving tool refers to a tool designed to relieve pressure on an ailing part by transferring support to healthy parts of an extremity, e.g., Thomas splint and the Voskoboinikova apparatus. Corrective tool refers to a tool designed to gradually correct a deformity, e.g., corsets, splints, orthopedic footwear, and insoles and other devices to correct abnormal positions of the foot. Compression-distraction tool refers to a tool designed to correct acquired or congenital deformities of the extremities, e.g., curvature, shortening, and pseudarthrosis such as Gudushauri. Fixation tools may be internal fixation tools (e.g., screws, plates) or external fixation tools (radius, tibia fracture fixation). Orthopedic tools may be bone-holding forceps, drill bits, nail pins, hammer staple, and the like. According to some embodiments, orthopedic tools can be utilized via the disclosed framework, discussed supra.

A drill refers to a tool for making holes in bones for insertion of implants like nails, plates, screws, and wires. The drill tool functions by drilling cylindrical tunnels into bone. Drill may be used in orthopedics for performing medical procedures. Use of drill on bones may have some risks harm caused to bone, muscle, nerves, and venous tissues are wrapped by surrounding tissue, the drill does not stop immediately. Drills vary widely in speed, power, and size. Drill may be powered as electrical, pneumatic, or battery. Drills generally may work on speed below 1000 rpm in orthopedic. Temperature control of drill is an important aspect in the functioning of drill and is dependent on parameters rotation speed, torque, orthotropic site, sharpness of the cutting edges, irrigation, cooling systems. The drill may consist of components physical drill, cord power, electronically motorized bone drill, rotating bone shearing incision work unit. According to some embodiments, a drill can be utilized via the disclosed framework, discussed supra.

A scalpel refers to a tool for slicing or cutting or osteotomy of bone during orthopedic procedure. The scalpel may be designed to provide clean cuts through osseous structures with minimal loss of viable bone while sparing adjacent elastic soft tissues largely unaffected while performing a slicing procedure. This is suited for spine applications where bone must be cut adjacent to the dura and neural structures. The scalpel does not rotate and performs cutting by an ultrasonically oscillating or forward/backward moving metal tip. Scalpel may prevent injuries caused by a drill in a spinal surgery such as complications such as nerve thermal injury, grasping soft tissue, tearing dura mater, and a mechanical injury may occur during drilling. According to some embodiments, a scalpel can be utilized via the disclosed framework, discussed supra.

Stitches (also referred to as sutures) refers to a sterile, surgical thread used to repair cuts or lacerations and are used to close incisions or hold body tissues together after a surgery or an injury. Stitches may involve the use of a needle along with an attached thread. Stitches may be of type absorbable (the stitches automatically break down harmlessly in the body over time without intervention) and non-absorbable (the stitches do not automatically break down over time and must be manually removed if not left indefinitely). Stitches may be of type based on material monofilament, multifilament, and barb. Stitches may be classified based on size. Stitches may be of type based on material synthetic and natural. Stitches may be of type based on coating coated and un-coated. According to some embodiments, stitches can be integrated into some embodiments in a variety of manners.

A stapler refers to a tool for fragment fixation when inter-fragmental screw fixation is not easy. When there is vast damage and bone is broken into fragments then staples can be used between these fragments for internal fixation and bone reconstruction. For example, they may be used around joints as in ankle and foot surgeries, in cases of soft tissue damage, to attach tendons or ligaments to the bone for reconstruction surgery. Stapler may be made of surgical grade stainless steel or titanium, and they are thicker, stronger, and larger. According to some embodiments, a stapler can be integrated into some embodiments in a variety of manners.

According to some embodiments, equipment refers to a set of articles, tools, or objects which help to implement or achieve an operation or activity. A medical equipment (or medical imaging equipment) refers to an article, instrument, apparatus, or machine used for diagnosis, prevention, or treatment of a medical condition or disease or detection, measurement, restoration, correction, or modification of structure/function of the body for some health purpose. The medical equipment may perform functions invasively or non-invasively. The medical equipment may consist of components sensor/transducer, signal conditioner, display, data storage unit, and the like. The medical equipment works by taking a signal from a measurand/patient, a transducer for converting one form of energy to electrical energy, signal conditioner such as an amplifier, filters, and the like, to convert the output from the transducer into an electrical value, display to provide a visual representation of measured parameter or quantity, a storage system to store data which can be used for future reference. A medical equipment may perform any function of diagnosis or provide therapy, for example, the equipment delivers air/breaths into the lungs and moves it out of the lungs and out of lungs, to a patient who is physically unable to breathe, or breaths insufficiently. According to some embodiments, medical equipment can be utilized via the disclosed framework, discussed supra.

A ventilator (also referred to as a respirator) refers to an instrument that provides a patient with oxygen when they are unable to breathe on their own. The ventilator is required when a person is not able to breathe on their own. The ventilator may perform a function of pushing air into the lungs and allows it to come back out, gently like lungs when they are working. Ventilator functions by delivery of positive pressure to force air into your lungs, while usual breathing uses negative pressure by the opening of the mouth, and air flows in. The machine uses positive pressure to force air into your lungs. A ventilator may be required during surgery or after surgery. A ventilator may be required in case of respiratory failure due to acute respiratory distress syndrome, head injury, asthma, lung diseases, drug overdose, neonatal respiratory distress syndrome, pneumonia, sepsis, spinal cord injury, cardiac arrest, and the like, or during surgery. The ventilator may be used with a face mask (non-invasive ventilation, where the ventilation is required for a shorter duration of time) or with a breathing tube also referred to as an endotracheal tube (invasive ventilation, where the ventilation is required for a longer duration of time). A ventilator use may have some risks such as infections, fluid build-up, muscle weakness, lung damage, and the like. A ventilator may be operated in modes ACV, SIMV, PCV, PSV, PCIRV, APRV, and the like. A ventilator may have components gas delivery system, power source, control system, safety feature, gas filter, monitor. According to some embodiments, a ventilator can be utilized via the disclosed framework, discussed supra.

Continuous positive airway pressure (CPAP) refers to an instrument which used for the treatment of sleep apnea disorder in a patient. Sleep apnea refers to a disorder in which breathing repeatedly stops and starts while a patient is sleeping, often because throat/airways briefly collapse or something temporarily blocks them and may lead to serious health problems, such as high blood pressure and heart trouble. Continuous positive airway pressure instrument helps the patient with sleep apnea to breathe more easily during sleep by sending a steady flow of oxygen into the nose and mouth during sleep, which keeps the airways open and helps to breathe normally. The CPAP machine may work by a compressor/motor which generates a continuous stream of pressurized air which travels through an air filter into a flexible tube. The tube delivers purified air into a mask sealed around the nose/mouth of the patient. The airstream from the instrument pushes against any blockages, opening the airways so lungs receive plenty of oxygen, and breathing does not stop as nothing obstructs oxygen. This helps the patient to not wake up to resume breathing. CPAP may have a nasal pillow mask, nasal mask, or full mask. CPAP instrument may consist of components a motor, a cushioned mask, a tube that connects the motor to the mask, a headgear frame, adjustable straps. The essential components may be a motor, a cushioned mask, a tube that connects the motor to the mask. According to some embodiments, CPAP instruments can be utilized via the disclosed framework, discussed supra.

Consumables refer to necessary supplies for health systems to provide care within a hospital or surgical environment. Consumables may include gloves, gowns, masks, syringes, needles, sutures, staples, tubing, catheters, and adhesives for wound dressing, in addition to other tools needed by doctors and nurses to provide care. Depending on the device mechanical testing may be carried out in tensile, compression or flexure, in dynamic or fatigue, or impact or with the application of torsion. Consumables may be disposable (are timesaving, no risk of healthcare-associated infections, cost-efficient) or sterilizable (cross-contamination, risk of surgical site infections, sterilization). According to some embodiments, consumables can be utilized via the disclosed framework, discussed supra.

Robotic systems refer to systems that provide intelligent services and information by interacting with their environment, including human beings, via the use of various sensors, actuators, and human interfaces. These are employed for automating processes in a wide range of applications, ranging from industrial (manufacturing), domestic, medical, service, military, entertainment, space, and the like. The adoption of robotic systems provides several benefits, including efficiency and speed improvements, lower costs, and higher accuracy. Performing medical procedures with the assistance of robotic technology are referred to as medical robotic systems. The medical robotic system market can be segmented by product type into surgical robotic systems, rehabilitative robotic systems, non-invasive radiosurgery robots, hospital & pharmacy robotic systems. Robotic technologies have offered valuable enhancements to medical or surgical processes through improved precision, stability, and dexterity. Robots in medicine help by relieving medical personnel from routine tasks, and by making medical procedures safer and less costly for patients. They can also perform accurate surgery in tiny places and transport dangerous substances. Robotic surgeries are performed using tele-manipulators, which use the surgeon's actions on one side to control the "effector" on the other side. A medical robotic system ensures precision and may be used for remotely controlled, minimally invasive procedures. The systems include computer-controlled electromechanical devices that work in response to controls manipulated by the surgeons. According to some embodiments, robotic systems can be utilized via the disclosed framework, discussed supra.

An electronic health record (EHR) refers to a digital record of a patient's health information, which may be collected and stored systematically over time. It is an all-inclusive patient record and could include demographics, medical history, history of present illness (HPI), progress notes, problems, medications, vital signs, immunizations, laboratory data, and radiology reports. A computer software is used to capture, store, and share patient data in a structured way. The EHR may be created and managed by authorized providers and can make health information instantly accessible to authorized providers across practices and health organizations—such as laboratories, specialists, medical imaging facilities, pharmacies, emergency facilities, and the like. The timely availability of EHR data can enable healthcare providers to make more accurate decisions and provide better care to the patients by effective diagnosis and reduced medical errors. Besides providing opportunities to enhance patient care, it may also be used to facilitate clinical research by combining all patients' demographics into a large pool. For example, the EHR data can support a wide range of epidemiological research on the natural history of disease, drug utilization, and safety, as well as health services research. According to some embodiments, EHRs can be utilized via the disclosed framework, discussed supra.

Equipment tracking systems, such as radio-frequency identification (RFID), for example, refers to a system that tags an instrument with an electronic tag and tracks it using the tag. Typically, this could involve a centralized platform that provides details such as location, owner, contract, and maintenance history for all equipment in real-time. A variety of techniques can be used to track physical assets, including RFID, global positioning system (GPS), Bluetooth low energy (BLE), barcodes, near-field communication NFC, Wi-Fi, and the like. The equipment tracking system include the hardware components, such as RFID tags, GPS trackers, barcodes, and QR codes. The hardware component is placed on the asset, and it communicates with the software (directly or via a scanner), providing it with data about the asset's location and properties. An equipment tracking system uses electromagnetic fields to transmit data from an RFID tag to a reader. Reading of RFID tags may be done by portable or mounted RFID readers. RFID may be very short for low frequency or high frequency for ultra-high frequency. Managing and locating important assets is a key challenge for tracking medical equipment. Time spent searching for critical equipment can lead to expensive delays or downtime, missed deadlines and customer commitments, and wasted labor. The problem has been solved by the use of barcode labels or using manual serial numbers and spreadsheets; however, these require manual labor. The RFID tag may be passive (smaller and less expensive, read ranges are shorter, have no power of their own, and are powered by the radio frequency energy transmitted from RFID readers/antennas) or active (larger and more expensive, read ranges are longer, have a built-in power source and transmitter of their own). Equipment tracking systems may offer advantages, no line of sight required, read Multiple RFID objects at once, scan at a distance, and flexibility. According to some embodiments, equipment tracking systems can be utilized via the disclosed framework, discussed supra.

Quantum computing refers to any computational device or method which utilizes properties of quantum states defined by quantum mechanics such as superposition, entanglement, and the like. to perform computations. These devices utilize qubits, which are the quantum equivalent to bits in a classical computing system, which include at least two quantum states or probable outcomes. These outcomes, combined with a coefficient representing the probability of each outcome, describes the possible states, or bits of data, which can be represented by the qubits according to the principle of quantum superposition. These states may be manipulated which may shift the probability of each outcome or additionally add additional possible outcomes to perform a calculation, the final state of which can be measured to achieve the result.

Quantum computing provides significant benefits in the areas of encryption and the simulation of natural systems. Encryption is aided by the uncertain nature of quantum computing in that data is represented by an indeterminate state of probable outcomes, therefore making decryption virtually impossible. The simulation of natural systems, such as chemical and biological interactions, benefit from the fact that nature of quantum computing is the same as the systems being simulated. In medical fields, quantum computing shows the greatest promise for drug discovery and simulating the interaction of drugs with biologic systems, however the same technology might be used to predict the interaction of a biologic system with an implanted device, preventing rejection of an implant by a patient's body, long term function of an implant, and potentially the reaction of a patient to a surgical procedure during a simulation before a procedure or actively during a procedure. Accordingly, quantum computing can be utilized via the disclosed framework, discussed supra.

Techniques operating according to the principles described herein may be implemented in any suitable manner. Included in the discussion above are a series of flow charts showing the steps and acts of various processes for analyzing movement information to determine a time at which to trigger acquisition of a medical image. The processing and decision blocks of the flow charts above represent steps and acts that may be included in algorithms that carry out these various processes. Algorithms derived from these processes may be implemented as software integrated with and directing the operation of one or more single- or multi-purpose processors, may be implemented as functionally-equivalent circuits such as a Digital Signal Processing (DSP) circuit or an Application-Specific Integrated Circuit (ASIC), or may be implemented in any other suitable manner. It should be appreciated that the flow charts included herein do not depict the syntax or operation of any particular circuit or of any particular programming language or type of programming language. Rather, the flow charts illustrate the functional information one skilled in the art may use to fabricate circuits or to implement computer software algorithms to perform the processing of a particular apparatus carrying out the types of techniques described herein. It should also be appreciated that, unless otherwise indicated herein, the particular sequence of steps and/or acts described in each flow chart is merely illustrative of the algorithms that may be implemented and can be varied in implementations and embodiments of techniques described herein.

Accordingly, in some embodiments, the techniques described herein may be embodied in computer-executable instructions implemented as software, including as application software, system software, firmware, middleware, embedded code, or any other suitable type of computer code. Such computer-executable instructions may be written using any of a number of suitable programming languages and/or programming or scripting tools, and may result from compiling of other code into machine language code or intermediate code that is interpreted by a framework or virtual machine for execution.

When techniques described herein are embodied as computer-executable instructions, these computer-executable instructions may be implemented in any suitable manner, including as a number of functional facilities, each providing one or more operations to complete execution of algorithms operating according to these techniques. A "functional facility," however instantiated, is a structural component of a computer system that, when integrated with and executed by one or more computers, causes the one or more computers to perform a specific operational role. A functional facility may be a portion of or an entire software element. For example, a functional facility may be implemented as a function of a process, or as a discrete process, as a thread of a process, or as any other suitable unit of processing. If techniques described herein are implemented as multiple functional facilities, each functional facility may be implemented in its own way; all need not be implemented the same way. Additionally, these functional facilities may be executed in parallel and/or serially, as appropriate, and may pass information between one another using a shared memory on the computer(s) on which they are executing, using a message passing protocol, or in any other suitable way.

Generally, functional facilities include functions, routines, programs, objects, components, data structures, etc. that perform particular tasks or implement particular abstract data types. Typically, the functionality of the functional facilities may be combined or distributed as desired in the systems in which they operate. In some implementations, one or more functional facilities carrying out techniques herein may together form a software package or software program application. These functional facilities may, in alternative embodiments, be adapted to interact with other, unrelated functional facilities and/or processes, to implement a software package or software program application.

Some examples of modules have been described herein, which may be implemented as one or more functional facilities for carrying out one or more tasks. It should be appreciated, though, that the modules and division of tasks described is merely illustrative of the type of functional facilities that may implement the exemplary techniques described herein, and that embodiments are not limited to being implemented in any specific number, division, or type of functional facilities. In some implementations, all functionalities may be implemented in a single functional facility. It should also be appreciated that, in some implementations, some of the functional facilities described herein may be implemented together with or separately from others (i.e., as a single unit or separate units), or some of these functional facilities may not be implemented.

Computer-executable instructions implementing the techniques described herein (when implemented as one or more functional facilities or in any other manner) may, in some embodiments, be encoded on one or more computer-readable media to provide functionality to the media. Computer-readable media include magnetic media such as a hard disk drive, optical media such as a Compact Disk (CD) or a Digital Versatile Disk (DVD), a persistent or non-persistent solid-state memory (e.g., Flash memory, Magnetic RAM, etc.), or any other suitable storage media. Such a computer-readable medium may be implemented in any suitable manner, including as computer-readable storage media 806 of FIG. 8 described below (i.e., as a portion of a computing device 800) or as a stand-alone, separate storage medium. As used herein, "computer-readable media" (also called "computer-readable storage media") refers to tangible storage media. Tangible storage media are non-transitory and have at least one physical, structural component. In a "computer-readable medium," as used herein, at least one physical, structural component has at least one physical property that may be altered in some way during a process of creating the medium with embedded information, a process of recording information thereon, or any other process of encoding the medium with information. For example, a magnetization state of a portion of a physical structure of a computer-readable medium may be altered during a recording process.

In some, but not all, implementations in which the techniques may be embodied as computer-executable instructions, these instructions may be executed on one or more suitable computing device(s) operating in any suitable computer system, including the exemplary computer system of FIG. 1A, or one or more computing devices (or one or more processors of one or more computing devices) may be programmed to execute the computer-executable instructions. A computing device or processor may be programmed to execute instructions when the instructions are stored in a manner accessible to the computing device or processor, such as in a data store (e.g., an on-chip cache or instruction register, a computer-readable storage medium accessible via a bus, a computer-readable storage medium accessible via one or more networks and accessible by the device/processor, etc.). Functional facilities comprising these computer-executable instructions may be integrated with and direct the operation of a single multi-purpose programmable digital computing device, a coordinated system of two or more multi-purpose computing device sharing processing power and jointly carrying out the techniques described herein, a single computing device or coordinated system of computing devices (co-located or geographically distributed) dedicated to executing the techniques described herein, one or more Field-Programmable Gate Arrays (FPGAs) for carrying out the techniques described herein, or any other suitable system.

Figure 8:
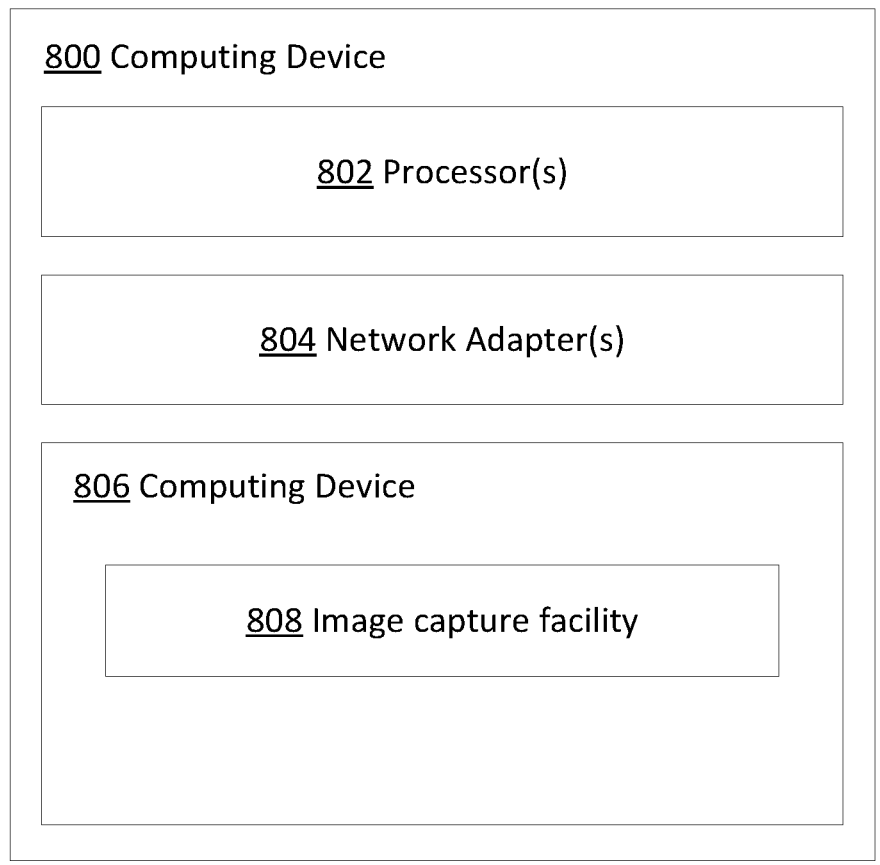
FIG. 8 is a block diagram illustrating a computing device showing an example of a client or server device used in various embodiments of the present disclosure.

FIG. 8 illustrates one exemplary implementation of a computing device in the form of a computing device 800 that may be used in a system implementing techniques described herein, although others are possible. It should be appreciated that FIG. 8 is intended neither to be a depiction of necessary components for a computing device to monitor movement and trigger medical image acquisition in accordance with the principles described herein, nor a comprehensive depiction.

Computing device 800 may comprise at least one processor 802, a network adapter 804, and computer-readable storage media 806. Computing device 800 may be, for example, a desktop or laptop personal computer, a personal digital assistant (PDA), a smart mobile phone, a server, a wireless access point or other networking element, or any other suitable computing device. Network adapter 804 may be any suitable hardware and/or software to enable the computing device 800 to communicate wired and/or wirelessly with any other suitable computing device over any suitable computing network. The computing network may include wireless access points, switches, routers, gateways, and/or other networking equipment as well as any suitable wired and/or wireless communication medium or media for exchanging data between two or more computers, including the Internet. Computer-readable media 806 may be adapted to store data to be processed and/or instructions to be executed by processor 802. Processor 802 enables processing of data and execution of instructions. The data and instructions may be stored on the computer-readable storage media 806.

The data and instructions stored on computer-readable storage media 806 may comprise computer-executable instructions implementing techniques which operate according to the principles described herein. In the example of FIG. 8, computer-readable storage media 806 stores computer-executable instructions implementing various facilities and storing various information as described above. Computer-readable storage media 806 may store an image capture facility 808 that may carry out one or more of the techniques described herein.

While not illustrated in FIG. 8, a computing device may additionally have one or more components and peripherals, including input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computing device may receive input information through speech recognition or in other audible format.

Embodiments have been described where the techniques are implemented in circuitry and/or computer-executable instructions. It should be appreciated that some embodiments may be in the form of a method, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Various aspects of the embodiments described above may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Use of ordinal terms such as "first," "second," "third," etc., in the claims to modify a claim element does not by itself connote any priority, precedence, or order of one claim element over another or the temporal order in which acts of a method are performed but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," "having," "containing," "involving," and variations thereof herein, is meant to encompass the items listed thereafter and equivalents thereof as well as additional items.

The word "exemplary" is used herein to mean serving as an example, instance, or illustration. Any embodiment, implementation, process, feature, etc. described herein as exemplary should therefore be understood to be an illustrative example and should not be understood to be a preferred or advantageous example unless otherwise indicated.

Having thus described several aspects of at least one embodiment, it is to be appreciated that various alterations, modifications, and improvements will readily occur to those skilled in the art. Such alterations, modifications, and improvements are intended to be part of this disclosure and are intended to be within the spirit and scope of the principles described herein. Accordingly, the foregoing description and drawings are by way of example only.

What is claimed is:

1. A method comprising:
    collecting, by a device, a first set of sensor data and a second set of sensor data using a wearable device associated with a patient, the first set of sensor data corresponding to positional movements performed by the patient during a first time period, the second set of sensor data corresponding to physical movements performed by the patient during a second time period;
    analyzing, by the device, the first set of sensor data and the second set of sensor data;
    determining, by the device, based on the analysis of the first and second sets of sensor data, a time to capture a medical image;
    triggering, by the device, an image capture operation to be performed by medical imaging equipment in accordance with the determined time, the medical imaging equipment connected to the device via a network, the image capture operation resulting in generation of the medical image;
    analyzing, by the device, the medical image;
    determining, by the device, a measure of quality of the medical image; and
    outputting, by the device, for display on a display associated with the medical imaging equipment, the medical image based on the determined measure of quality.

2. The method of claim 1, further comprising:
    determining, based on the analysis of the first set of sensor data, positional movement data corresponding to the positional movements of the patient;
    analyzing the positional movement data; and
    determining a quantity of positional movement of the patient.

3. The method of claim 2, further comprising:
    comparing the quantity of positional movement to a movement threshold; and
    determining whether the patient is being repositioned during the first time period based on the comparison, wherein the determined time for capture is based on the determination of the patient being repositioned.

4. The method of claim 1, further comprising:
    determining, based on the analysis of the second set of sensor data, physical movement data corresponding to the physical movements of the patient;
    analyzing the physical movement data; and
    determining a pattern of the physical movements, the pattern comprising indications of an activity range of physical movements, wherein the determined time for capture is based on the activity range of physical movements.

5. The method of claim 4, further comprising:
    determining, based on the analysis of the medical image and/or the determined measure of quality in accordance with one or more quality criteria, whether the medical image satisfies the one or more quality criteria; and
    in response to determining that the medical image does not satisfy the one or more quality criteria, triggering another image capture to be performed by the medical imaging equipment to generate another medical image.

6. The method of claim 1, further comprising:
    storing, as a data entry in at least one associated database, information related to the first set of sensor data, the second set of sensor data and the captured medical image, the at least one associated database comprising a plurality of data entries for a plurality of medical images.

7. The method of claim 6, further comprising:
    extracting, from the at least one associated database, each data entry of the plurality of data entries;
    analyzing, for each data entry, a respective medical image;
    determining, for each respective medical image, a confidence score; and
    ranking, based on the determined confidence scores, the medical images.

8. The method of claim 7, further comprising:
    identifying, based on the ranking of medical images, a first medical image;
    causing display of the first medical image; and
    determining whether the first medical image has been approved.

9. The method of claim 8, wherein a second medical image within the ranking of medical images is displayed in response to determining that the first medical image has been disapproved.

10. The method of claim 8, wherein a set of medical images are identified and output for display.

11. The method of claim 1, further comprising:
identifying a location of the wearable device, the location corresponding to a position on the patient, wherein the collection of the first and second set of sensor data is based on location data corresponding to the identified location.

12. The method of claim 1, further comprising:
identifying a plurality of wearable devices, each wearable device of the plurality of wearable devices being positioned on a different part of the patient, wherein the image capture of the medical image is based on sensor data from each of the plurality of wearable devices.

13. The method of claim 1, wherein the medical imaging equipment is selected from a group of machines consisting of: magnetic resonance imaging (MRI), computed tomography (CT), X-ray, positron emission tomography (PET), ultrasound, angiography, fluoroscopy and myelography.

14. A device comprising:
at least one processor; and
at least one storage medium having encoded thereon executable instructions that, when executed by the at least one processor, cause the at least one processor to carry out a method comprising:
identifying a wearable device associated with a patient, the wearable device comprising functionality associated with at least one sensor;
collecting a first set of sensor data and a second set of sensor data from the at least one sensor of the wearable device, the first set of sensor data corresponding to positional movements performed by the patient during a first time period, the second set of sensor data corresponding to physical movements performed by the patient during a second time period;
analyzing the first set of sensor data and the second set of sensor data;
determining, based on the analysis of the first and second sets of sensor data, a time to capture a medical image;
triggering an image capture operation to be performed by medical imaging equipment in accordance with the determined time, the medical imaging equipment connected to the device via a network, the image capture operation resulting in generation of the medical image;
analyzing the medical image;
determining a measure of quality of the medical image; and
outputting, for display on a display associated with the medical imaging equipment, the medical image based on the determined measure of quality.

15. The device of claim 14, wherein the method further comprises:
determining, based on the analysis of the first set of sensor data, positional movement data corresponding to the positional movements of the patient;
analyzing the positional movement data;
determining a quantity of positional movement of the patient;
comparing the quantity of positional movement to a movement threshold; and
determining whether the patient is being repositioned during the first time period based on the comparison, wherein the determined time for capture is based on the determination of the patient being repositioned.

16. The device of claim 14, wherein the method further comprises:
determining, based on the analysis of the second set of sensor data, physical movement data corresponding to the physical movements of the patient;
analyzing the physical movement data;
determining a pattern of the physical movements, the pattern comprising indications of an activity range of physical movements, wherein the determined time for capture is based on the activity range of physical movements;
determining, based on the analysis of the medical image in accordance with a quality threshold, that the quality of the medical image does not correspond to a high-quality image; and
triggering another image capture to be performed, such that another medical image is generated based on the quality determination.

17. The device of claim 14, wherein the method further comprises:
store, in at least one associated database, as a data entry, information related to the first set of sensor data, the second set of sensor data and the captured medical image, the at least one associated database comprising a plurality of data entries for a plurality of medical images;
extract, from the at least one associated database, each data entry of the plurality of data entries;
analyze, for each data entry, a respective medical image;
determine, for each respective medical image, a confidence score; and
rank, based on the determined confidence scores, the medical images.

18. The device of claim 17, wherein the method further comprises:
identifying, based on the ranking of medical images, a first medical image;
outputting for display the first medical image;
determining whether the first medical image has been approved; and
in response to determining that the first medical image has been disapproved, outputting for display a second medical image within the ranking of medical images.

19. At least one non-transitory computer-readable storage medium tangibly encoded with computer-executable instructions that, when executed by a device, cause the device to perform a method comprising:
identifying, by the device, a wearable device associated with a patient, the wearable device comprising functionality associated with at least one sensor;
collecting, by the device, a first set of sensor data and a second set of sensor data from the at least one sensor of the wearable device, the first set of sensor data corresponding to positional movements performed by the patient during a first time period, the second set of sensor data corresponding to physical movements performed by the patient during a second time period;
analyzing, by the device, the first set of sensor data and the second set of sensor data;
determining, by the device, based on the analysis of the first and second sets of sensor data, a time to capture a medical image;
triggering, by the device, an image capture operation to be performed by medical imaging equipment in accordance with the determined time, the medical imaging equipment connected to the device via a network, the image capture operation resulting in generation of the medical image;

analyzing, by the device, the medical image;
determining, by the device, a measure of quality of the medical image; and
outputting, by the device, for display on a display associated with the medical imaging equipment, the medical image based on the determined measure of quality.

20. The at least one non-transitory computer-readable storage medium of claim 19, further comprising:
storing, in at least one associated database, as a data entry, information related to the first set of sensor data, the second set of sensor data and the captured medical image, the at least one associated database comprising a plurality of data entries for a plurality of medical images;
extracting, from the at least one associated database, each data entry of the plurality of data entries;
analyzing, for each data entry, a respective medical image;
determining, for each respective medical image, a confidence score; and
ranking, based on the determined confidence scores, the medical images;
identifying, based on the ranking of medical images, a first medical image;
causing display of the first medical image; and
determining an approval of the first medical image, wherein a second medical image within the ranking of medical images is displayed upon disapproval of the first medical image.

* * * * *